(12) United States Patent
Radgowski et al.

(10) Patent No.: US 7,736,335 B2
(45) Date of Patent: Jun. 15, 2010

(54) PRESSURE WEDGE IRRIGATION PUMP

(75) Inventors: Todd J. Radgowski, San Jose, CA (US); Reid S. Cover, Mountain View, CA (US)

(73) Assignee: Stryker Corporation, Kalamazoo, MI (US)

( * ) Notice: Subject to any disclaimer, the term of this patent is extended or adjusted under 35 U.S.C. 154(b) by 1372 days.

(21) Appl. No.: 11/146,870

(22) Filed: Jun. 7, 2005

(65) Prior Publication Data

US 2006/0285986 A1 Dec. 21, 2006

(51) Int. Cl.
 *A61M 1/00* (2006.01)
 *A61M 31/00* (2006.01)
(52) U.S. Cl. .......................................... 604/153; 604/67
(58) Field of Classification Search ................ 604/65, 604/67, 118, 131, 132, 151, 153, 890.1; 128/DIG. 12, 128/DIG. 13
 See application file for complete search history.

(56) References Cited

U.S. PATENT DOCUMENTS

| | | | | |
|---|---|---|---|---|
| 3,335,724 | A | * | 8/1967 | Gienapp ..................... 604/152 |
| 4,353,367 | A | * | 10/1982 | Hunter et al. ............... 604/275 |
| 5,330,431 | A | | 7/1994 | Herskowitz |
| 5,342,313 | A | | 8/1994 | Campbell et al. |
| 5,348,539 | A | * | 9/1994 | Herskowitz ................. 604/153 |
| 5,399,166 | A | | 3/1995 | Laing |
| 5,423,759 | A | | 6/1995 | Campbell |
| 5,893,843 | A | | 4/1999 | Claro |

FOREIGN PATENT DOCUMENTS

| | | |
|---|---|---|
| EP | 1 086 713 A2 | 3/2001 |
| WO | WO 95/01194 | 1/1995 |

OTHER PUBLICATIONS

International Preliminary Report on Patentability and Written Opinion dated Dec. 11, 2007.
International Search Report and Written Opinion mailed Jan. 19, 2007 in International Appln. No. PCT/US2006/022203.

* cited by examiner

*Primary Examiner*—Nicholas D Lucchesi
*Assistant Examiner*—Nathan R Price
(74) *Attorney, Agent, or Firm*—Flynn, Thiel, Boutell & Tanis, P.C.

(57) ABSTRACT

A pump for rapidly discharging irrigation fluid to a surgical site. The pump includes a cabinet with an opening. Inside the pump there is a static plate and a dynamic plate that extends towards/retracts from the static plate. The space between the plates is a bag well in which a bag containing irrigation fluid can be inserted/replaced through the cabinet opening. A lid covers the opening. A sensor monitors the open/closed state of the lid. A drive motor actuates the dynamic plate. A control unit regulates the actuation of the motor. Only when the lid sensor determines that the lid is closed does the control unit actuate the motor. The dynamic plate can be placed in various open positions relative to the static plate so bags containing different volumes of fluid can be used with the pump.

29 Claims, 26 Drawing Sheets

PRESSURE WEDGE IRRIGATION PUMP

FIELD OF THE INVENTION

This invention is generally related to a pressure wedge irrigation pump useful for supplying irrigating fluid during a surgical or medical procedure. More particularly, this invention is related to a pressure wedge irrigation pump that does not need to be attached to a external power source in order to be actuated, to which and from which it is a relatively easy task to install and replace bags and that provides a quick, readily seen indication of the amount of fluid that is left in the attached bag.

BACKGROUND OF THE INVENTION

During the course of certain medical and surgical procedures, there is sometimes a need to provide a relatively high volume flow of irrigating fluid to the site of the body of the patient at which the procedure is being performed. For example, sometimes this fluid flow is required during the performance of an endoscopic surgical procedure. In an endoscopic surgical procedure, an elongated tube is directed to a surgical site within a patient through an opening called a portal. Other surgical instruments are directed to the surgical site through other portals. The surgeon views the surgical site through the endoscope. Based on the image viewed, the surgeon manipulates the other surgical instruments in order to perform the desired surgical procedure. In an endoscopic surgical procedure, as opposed to an open cut procedure, less of the patient's body is cut open to access the surgical site. This minimal opening of the patient's body both lessens the extent to which the patient's internal organs and tissue are open to infection and the extent to which the patient has to heal after surgery.

Two types of endoscopic surgical procedures are laparoscopic procedures and arthroscopic procedures. In a laparoscopic surgical procedure, a specialized type of endoscope, a laparoscope, and companion surgical instruments are used to perform minimally invasive surgery within the abdominal cavity of the patient. In a laparoscopic surgical procedure, it is sometimes necessary to provide a large volume of irrigating fluid to wash out and clear the surgical site. An arthroscopic surgical procedure is a procedure that is performed endoscopically on the musculo-skeletal system of the patient. In an arthroscopic surgical procedure, it is sometimes necessary to provide a large volume of irrigating fluid in order to distend the tissue at the surgical site and/or to clear away debris from the surgical site.

Many high volume irrigation pumps presently available are constructed to have what are referred to as pressure closets. A pressure closet is a space that is typically located between the front face of the pump and a complementary lid. Internal to the pump is an inflatable bladder that expands into the pressure closet. This pump is used by placing a bag containing the irrigating fluid into the pressure closet. When irrigating fluid is desired, compressed air is supplied to the bladder to cause its expansion into the pressure closet and against the bag. The action of the bladder working against the bag compresses the bag so as to force the fluid in the bag out of the pump, through an attached tube and into the patient. Thus, by using pumps of this type, a flow of sterile fluid at flow rates traditionally between, for example, 3.0 lt./min. and 4.5 lt./min., can be obtained.

There are some disadvantages associated with the presently available pumps used to provide the above flow rates. For example, as mentioned above, many of the presently available pumps function by inflating a bladder integral with the pump. The air used to inflate this bladder is supplied from the hospital's internal air supply source. Thus, whenever use of this type of pump is required during a surgical procedure, an air line must be connected between an outlet in the surgical suite and a complementary inlet on the pump. The introduction of this air line into the surgical suite adds to the overall clutter in the suite that the surgical staff needs to avoid. Additionally, special adapters are needed to connect with various surgical suite outlets.

Moreover, in order to set up many popular pumps for operation the staff must: insure the air line is connected to the wall outlet; open the door to the pressure closet; hang the bag; shut the door; latch the door shut; set the desired pressure; and actuate a power switch. Once a bag is emptied, the staff must unlock the door and open it in order to remove the bag. Requiring the surgical staff to perform all these different steps makes both mounting the bag in the pump and then removing the empty bag a time-consuming process.

Moreover, many current pumps are provided with transparent doors to their pressure closets. In theory, this type of door allows the surgical staff to look at a bag to visually determine the extent to which it has been emptied. However, as a consequence of the bag being pressed against the door, and the fact that both the bag and the fluid are transparent, it is often difficult to quickly determine the volume of fluid in a partially emptied bag. Surgical personnel are often left with two options if it is not immediately clear how much fluid remains. First, the personnel may have to temporarily stop performing the surgical procedure and focus their attentions on accurately determining the extent to which the bag has been emptied.

Alternatively, the personnel can continue performing the surgical procedure based on an estimate that the bag contains a sufficient amount of fluid for the next time a high volume discharge of fluid is required.

In order to facilitate the efficient use of surgical supplies, bags containing different volumes of the sterile fluid are available. Two of the most popular sized bags contain either 1 lt. or 3 lt. of fluid. Unfortunately, many presently available pumps are designed to force fluid out of a single size of bag. In order to reduce the amount of equipment in an operating room, typically, only a single pump is present. If, for a particular procedure, only a pump for a 1 lt. bag is available and large amounts of fluid are required, the surgical personnel will then have to spend an inordinate amount of time removing empty bags and replacing them with full ones. If, for a particular procedure, a 3 lt. bag pump is provided and only a relatively small volume of fluid is required, the unspent contents of the bag will, after the procedure, go to waste.

SUMMARY OF THE INVENTION

This invention relates to a new and useful pump for supplying irrigating fluid to a surgical site at a relatively high flow rate. The pump of this invention has a rechargeable battery built into the pump that supplies the power to actuate the pump. In most situations, this eliminates the need to provide a cord or line that runs from the wall of the operating room to the pump when the pump is being used. The pump of this invention is further constructed so that both fitting a full bag to the pump and removing the spent bag are relatively simple tasks that can be performed quickly.

The pump of this invention has a visual fluid level indicator that can be quickly checked to determine the extent to which an attached bag has been emptied. The pump of this invention is further designed so as to readily accept bags that contain different volumes of irrigating fluid and to operate appropriately based on the size of the supplied bag.

BRIEF DESCRIPTION OF THE DRAWINGS

The invention is pointed out with particularity in the claims. The above and further features and advantages of the pump of this invention may be better understood by reference to the accompanying Detailed Description taken in conjunction with the following drawings in which:

DETAILED DESCRIPTION

Figure 1:
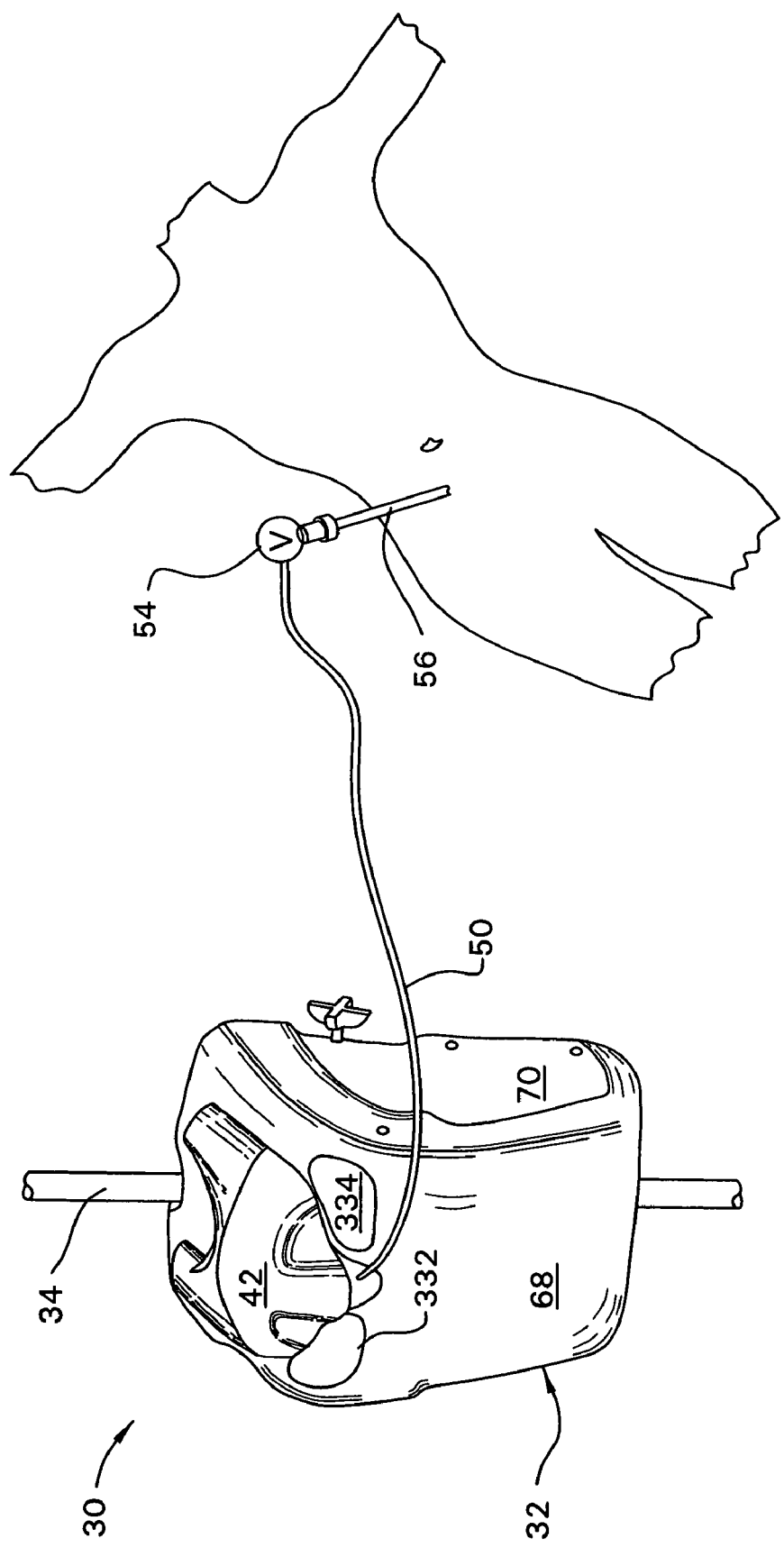
FIG. 1 is a perspective view of the pump of this invention.
Figure 2:
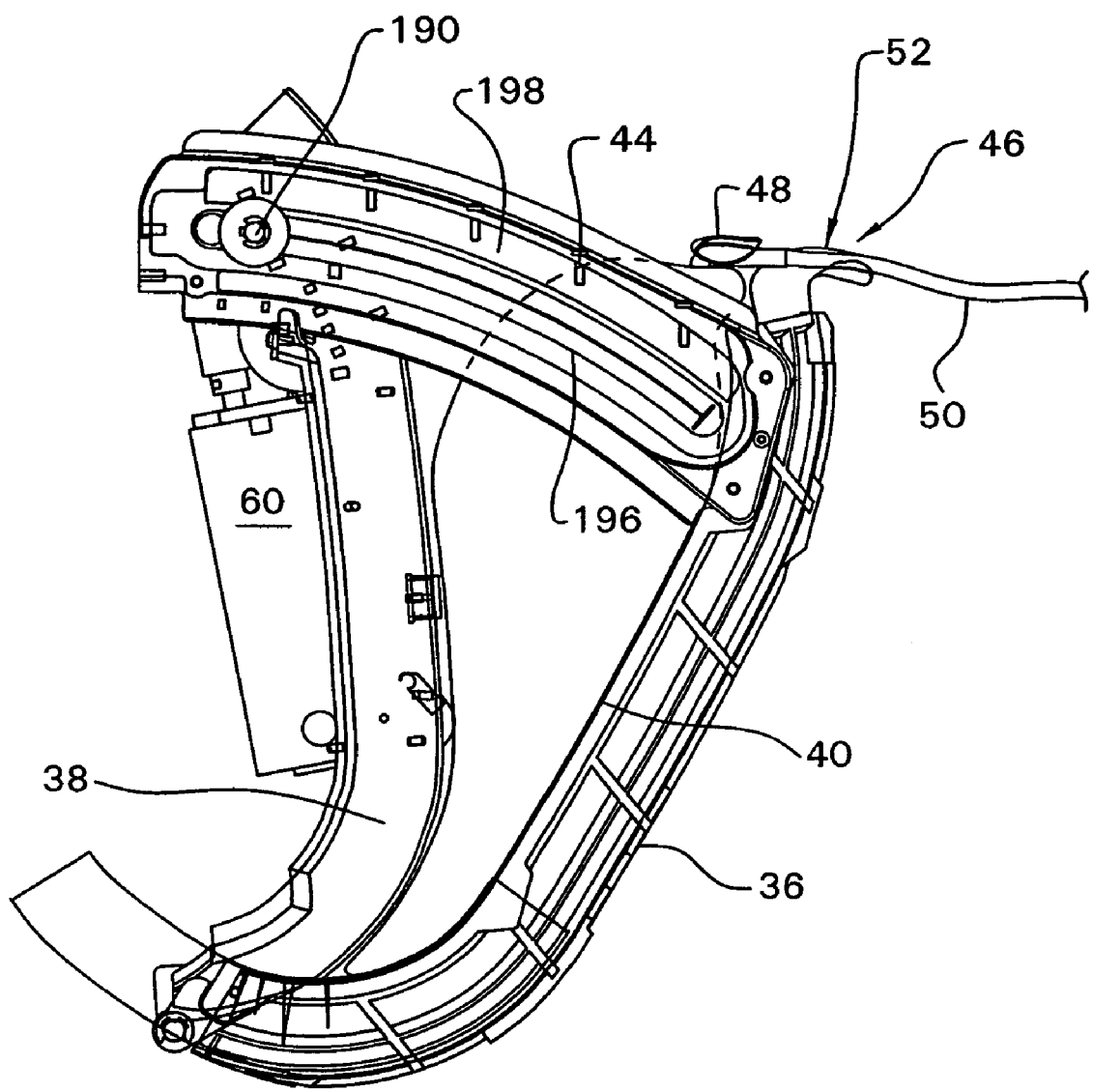
FIG. 2 is a side view of the components internal to the pump of this invention.
Figure 3:
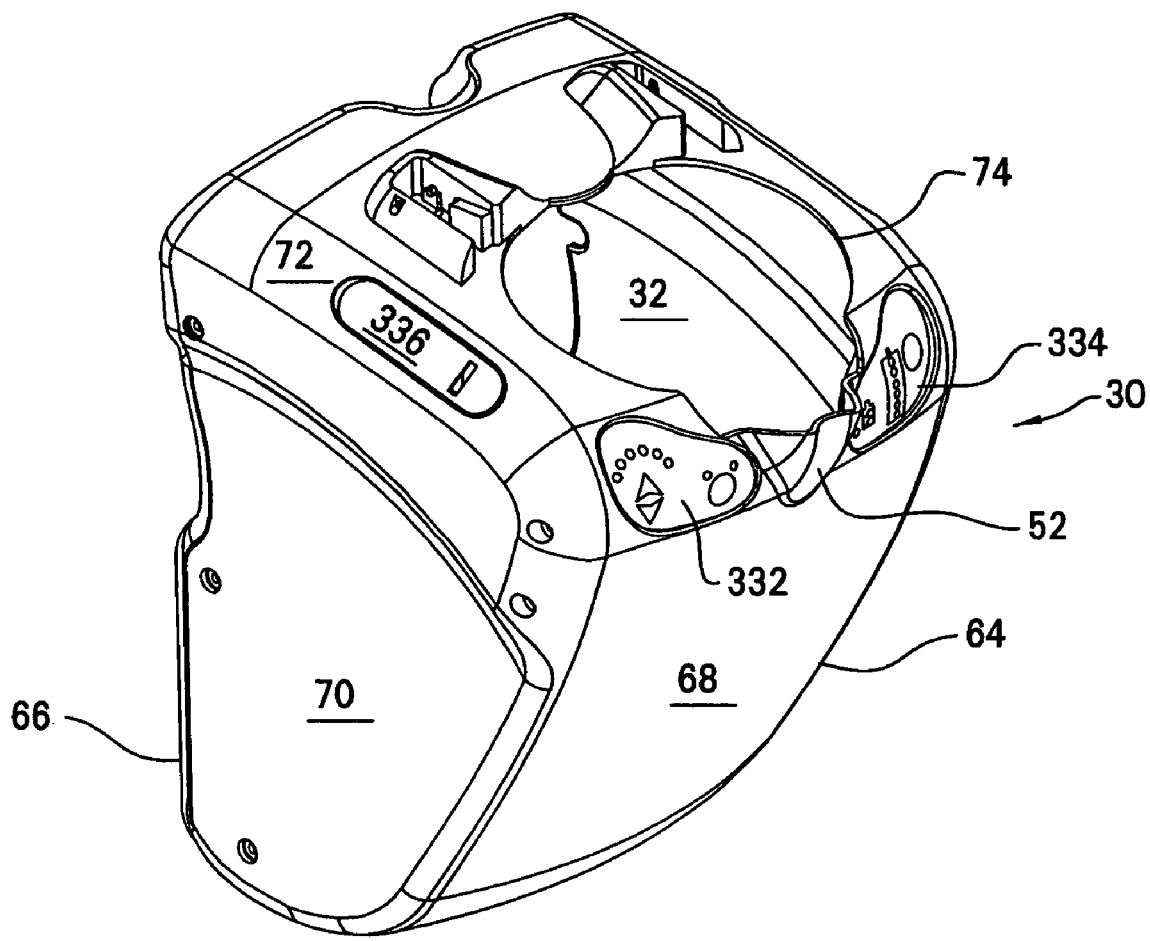
FIG. 3 is a perspective view of the front of the cabinet of the pump of this invention, wherein the lid is removed.

As seen by reference to FIG. 1-3, pump 30 of this invention includes a cabinet 32 that is mounted to a conventional IV pole 34. Internal to cabinet 32 and located immediately inside of the front wall of the case is an immobile static plate 36. Pump 30 also has a dynamic plate 38 located inwardly of the static plate 36. The lower end of the dynamic plate 38 is pivotally attached to the static plate 36. More particularly, the dynamic plate 38 is pivotally attached to static plate 36 so as to be able to extend towards and retract away from the adjacent inwardly directed face of the static plate 36.

The space between plates 36 and 38 is referred to as a bag well 40. A lid 42 that is pivotally attached to the top of cabinet 32 is selectively opened to allow access to the bag well 40. The pump 30 of this invention is prepared for use by placing a bag 44 of sterile solution in the bag well 40. A tube set 46 is connected to the bag 44. More particularly, the tube set 46 has a spike 48 that is used to establish a puncture opening in the bag 44. An outflow tube 50, part of the tube set 46, extends outwardly from a spout 52 integral with spike 48. A valve 54, shown diagrammatically, is in-line with the outflow tube 50. Valve 54 regulates fluid flow out of outflow tube 50. The distal end of the outflow tube 50, the end downstream from valve 54, is connected to a cannula 56. The discharged fluid is introduced into the body of the patient through the cannula 56.

As seen by FIG. 2, the pump 30 has a motor 60 that is connected to the dynamic plate 38 for extending and retracting the dynamic plate. A controller, described and illustrated below, regulates the actuation of the motor 60. More particularly, upon the closing of the lid 42, the pump is available for use. The opening of the valve 54 allows fluid flow out of the bag 44 and tube 50. This results in actuation of the motor 60. The extension of the dynamic plate 38 compresses the bag 44 between the plates 36 and 38 so as to force fluid out of the bag 44 through outflow tube 50 to the surgical site. When the dynamic plate 38 is fully extended so as to be in its closest position adjacent the static plate 36, the bag 44 has been emptied. Once the dynamic plate 38 reaches this position, the controller actuates the motor 60 so as to cause the motor to retract the dynamic plate 38 back away from the static plate 36. The controller also actuates a solenoid 314 (FIG. 24) so as to cause lid 42 to pop open. The pump 30 of this invention is thus in a position in which the empty bag 44 can quickly be removed and a new full bag 44 easily fitted in place.

Figure 4:
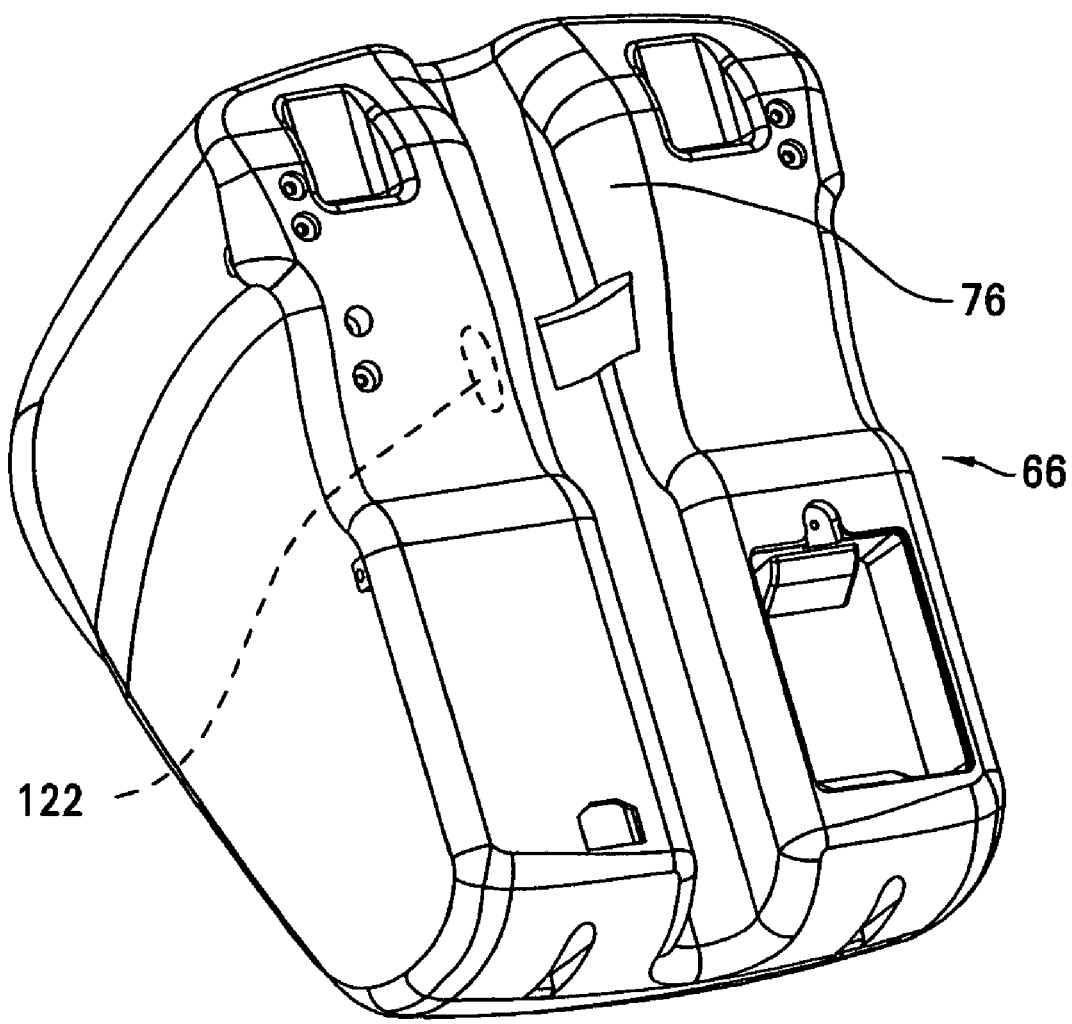
FIG. 4 is a perspective view of the rear of the cabinet of this invention, wherein the lid over the battery compartment is removed.
Figure 5:
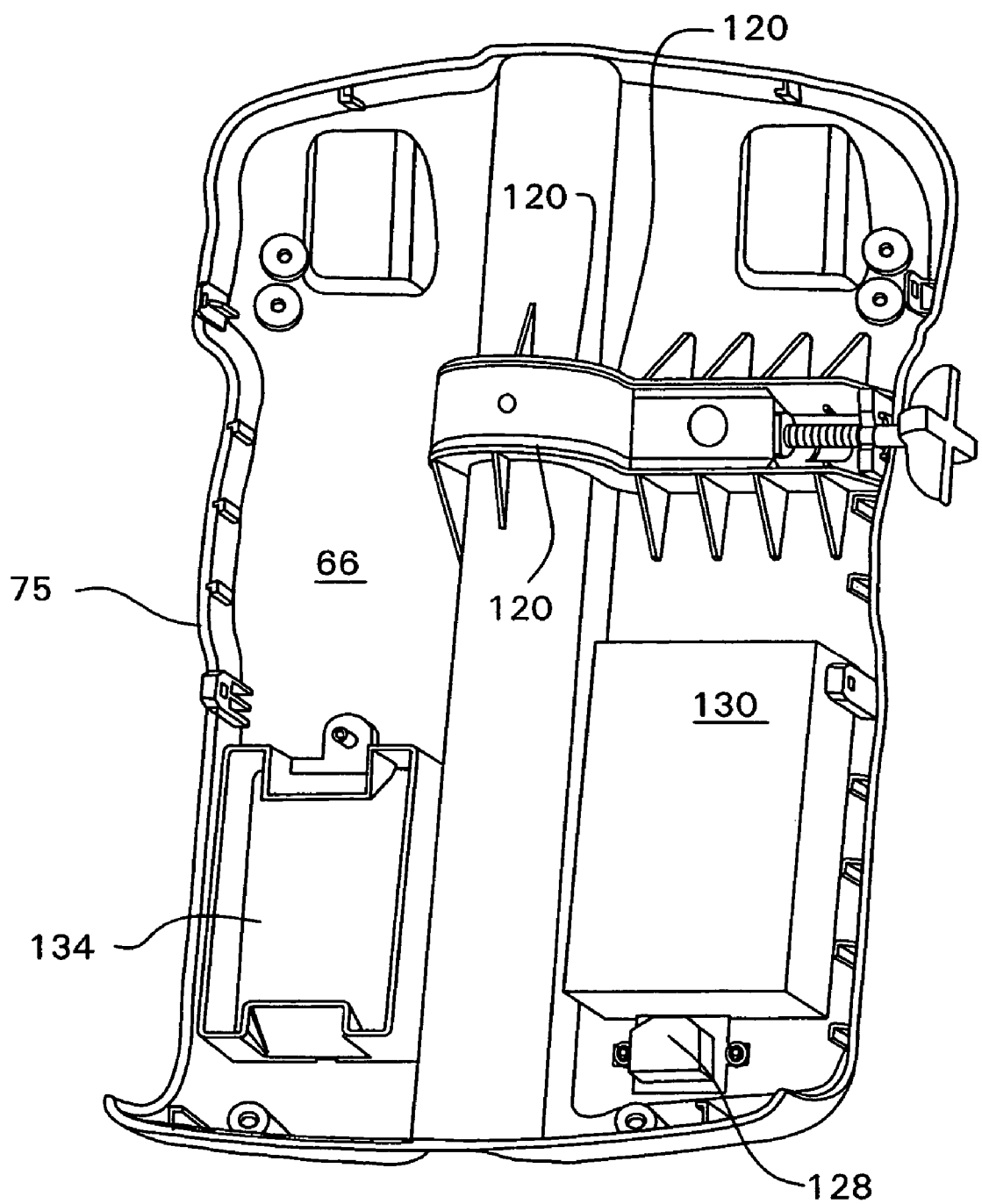
FIG. 5 is a perspective view inner surface of the cabinet back panel.

As seen by reference to FIGS. 3-5, the pump cabinet 32 consists of two sections, a front piece 64 and a back piece 66. The cabinet front piece 64 is shaped to have a front panel 68 that, from the top, is inwardly angled. Two opposed side panels 70 that are integral with and located on opposed sides of the front panel 68 also form part of the cabinet front piece 64. The cabinet front piece 64 also has a top panel 72 that extends between the side panels and that extends to the front panel 68. The top panel 72 is formed with a rim 74 that defines an opening into bag well 40.

The cabinet back piece 66 is generally a planar structure. The back piece 66 is formed with a circumferential lip 75 to facilitate the mating of the back piece 66 to the front piece 64. Cabinet back piece 66 is also formed to define a longitudinal groove 76 that extends along the whole of the longitudinal axis of the back piece 66. When the pump 30 is mounted to the IV pole 34, the pole seats in groove 76.

Figure 6:
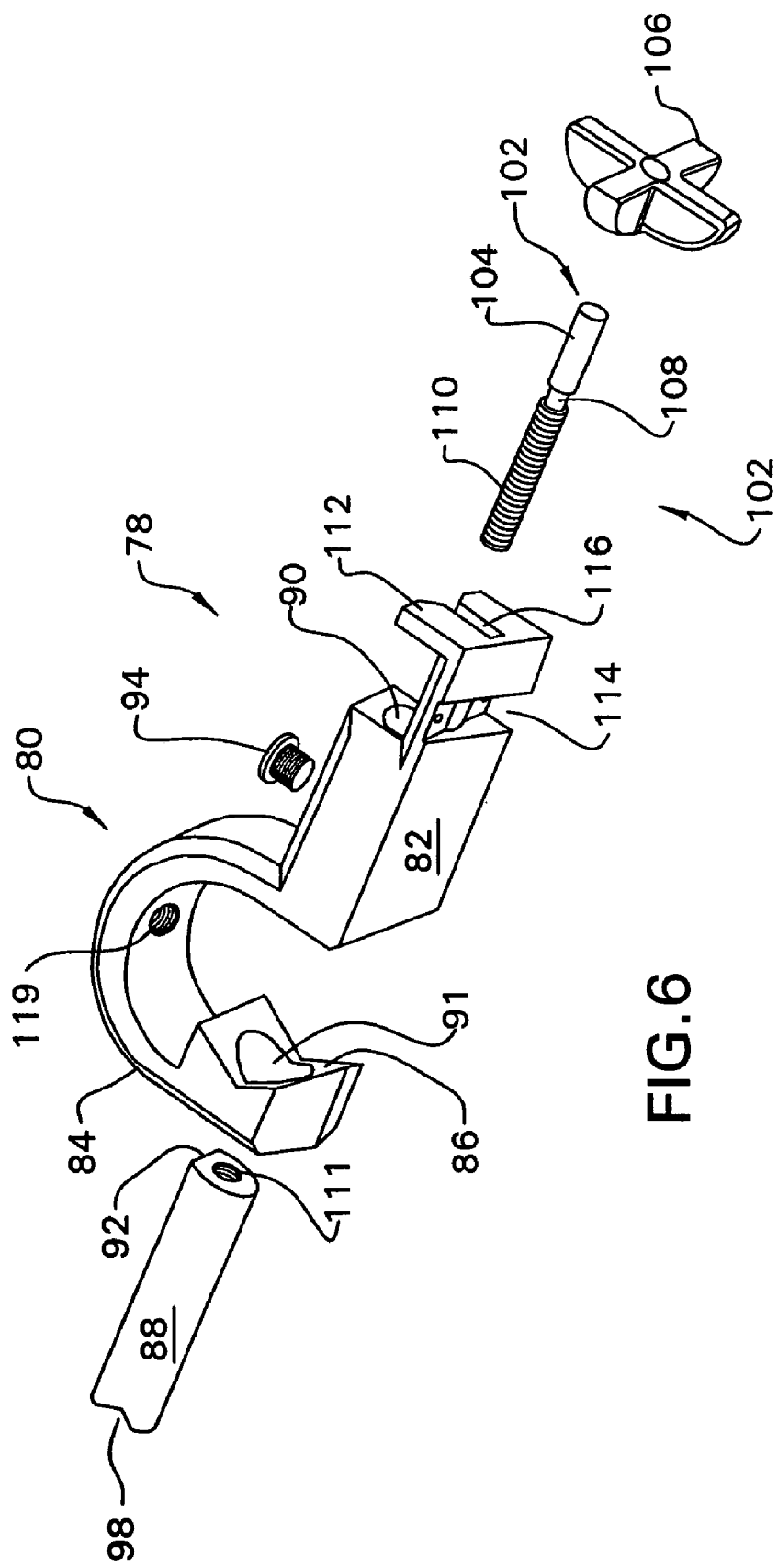
FIG. 6 is an exploded view of the components forming the clamp assembly.

A clamp assembly 78, now described by reference to FIG. 6 releasably holds the pump 30 to pole 34. The clamp assembly 78 includes a clamp body 80. The clamp body 80 has an elongated stem 82 from which a C-shaped head 84 extends. The end of the head 84 opposite the end of stem 82 is formed to have a V-shaped nose 86 that is directed towards stem 82.

A sleeve shaped clamp jaw 88 is slidably fitted into an elongated bore 90 that extends longitudinally axially through body stem 82. The clamp jaw 88, it will be observed, is formed so as to have a flat 92 that extends laterally along the outer surface. When clamp assembly 78 is assembled, an anti-rotation pin 94 that extends perpendicularly through body stem 82 presses against flat 92 to prevent the jaw 88 from rotating. The front end of the jaw 92 is formed to have a small V-shaped groove 98. When clamp assembly 78 holds the pump 30 to pole 34, the surfaces of body nose 86 and of the jaw 88 that define groove 98 are the surfaces that press against the pole.

The movement of clamp jaw 88 towards and away from body nose 86 is controlled by a lead screw 102. Lead screw 102 has a head 104 to which a clamp handle 106 is securely attached. Beyond the head 104, lead screw 102 has a neck 108 of reduced diameter than the head. The distal end of the lead screw 102, the end beyond neck 108, is formed to have a threaded section 110. The lead screw threaded section 110 engages complementary threading formed on the inner wall of the bore 111 that extends longitudinally through clamp jaw 88.

Extending outwardly from the front end of the stem 82, clamp body is formed to have an L-shaped foot 112 that extends out of the end of the stem. It can further be seen how the clamp body is formed so that a section of the foot 112 immediately adjacent the stem has a reduced depth so as to define a recess 114. Foot 112 is formed to have a slot 116 in line with the opening into stem bore 90. Clamp assembly 78 is assembled so that the lead screw neck 108 seats in foot slot 116. The foot 112 thus prevents longitudinal movement of the lead screw 102.

The clamp assembly 78 is disposed between two parallel, spaced apart webs 120 that extend outwardly from the inner face of the cabinet back piece 66. Body recess 114 seats over a mounting block formed in the back piece 66 between the webs 120 (mounting block not shown). Threaded fasteners (not identified) extend through the mounting block so as to hold the clamp body 80 and, by extension the whole of the clamp assembly 78, to the back piece 66. The portion of the back piece that defines groove 76 is formed with two opposed openings 122 and 124 that open into the groove and that are longitudinally aligned with the clamp body 80. The clamp body nose 86 extends through opening 122. Clamp jaw 88 extends through the opposed opening 124.

The pump 30 is secured to pole 34 by rotating handle 106 and, by extension, lead screw 102. The rotation of lead screw 102 causes the jaw 88 to move forward, towards clamp body nose 86. Consequently, the pole 34 is compression secured between clamp body nose 86 and jaw 88.

Figure 26:
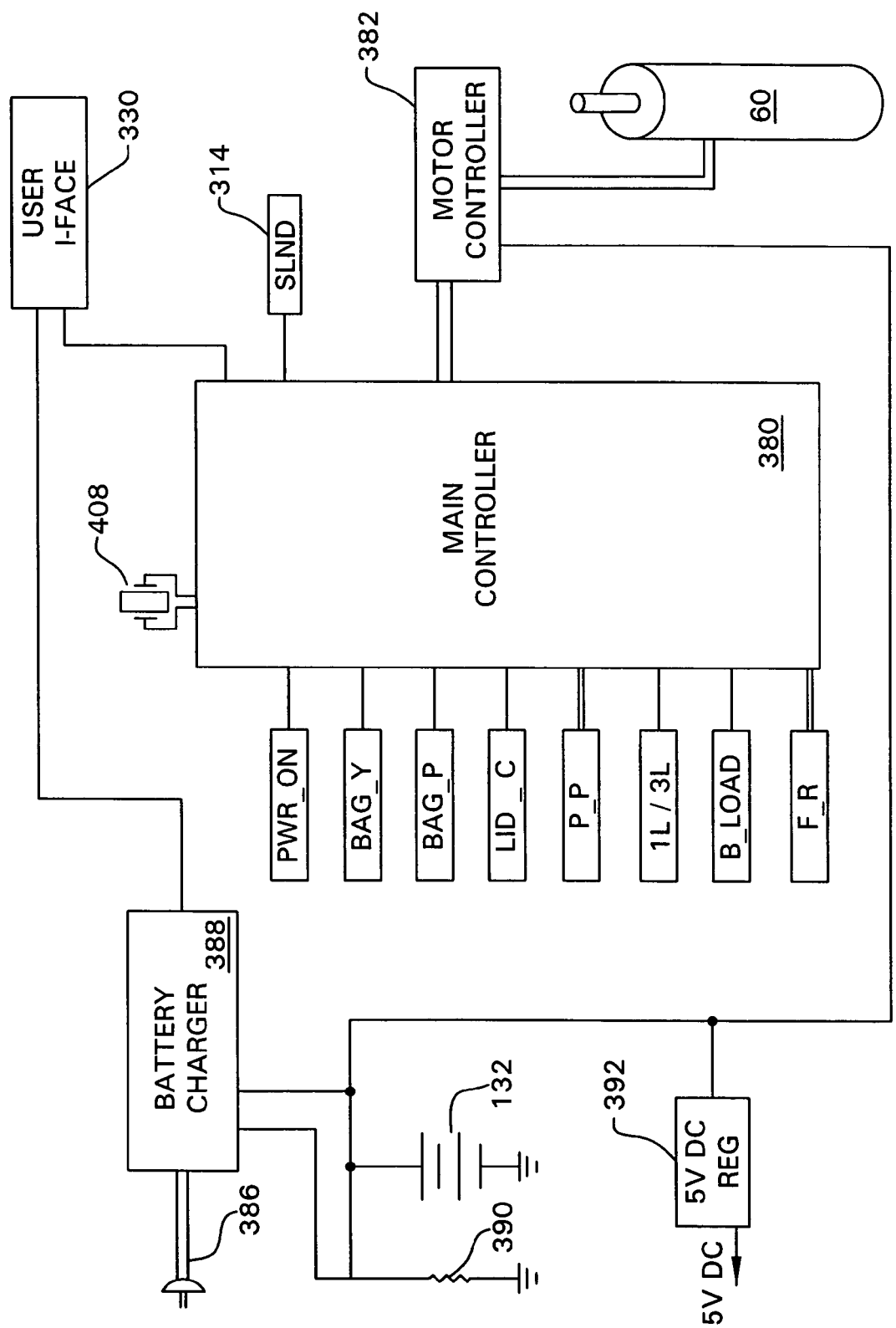
FIG. 26 is a block and partial schematic diagram of the primary electrical components of the pump of this invention.

A power socket 128 for receiving a line cord is secured to a lower portion of back piece 66. The current received through socket 128 is applied to a power supply 130 secured to the inner surface of back piece 66 above the socket 128. The power supply 130 is used to energize a set of rechargeable batteries 132 (FIG. 26). Often, Lithium Ion cells are employed as batteries 132. Typically, sufficient Lithium Ion cells 132 are provided that can discharge a 24 VDC signal at 5 Amps. The batteries 132 are accessible through an opening 134 in the cabinet back piece 66 opposite socket 128. A removal lid (not illustrated) normally covers opening 134.

The structure of the power supply 130 is discussed in further detail below.

Figure 7:
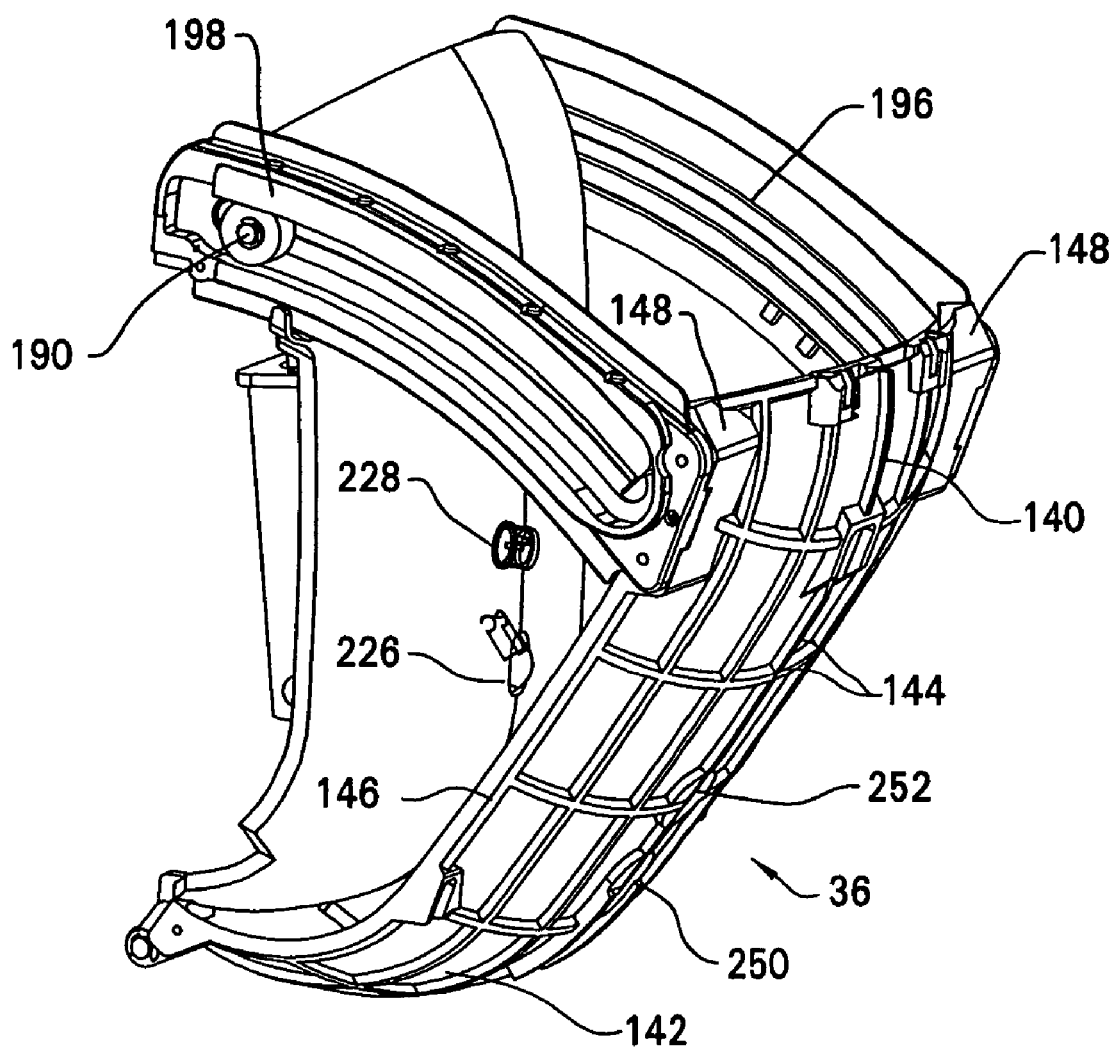
FIG. 7 is a perspective view of the static plate and dynamic plate.
Figure 8:
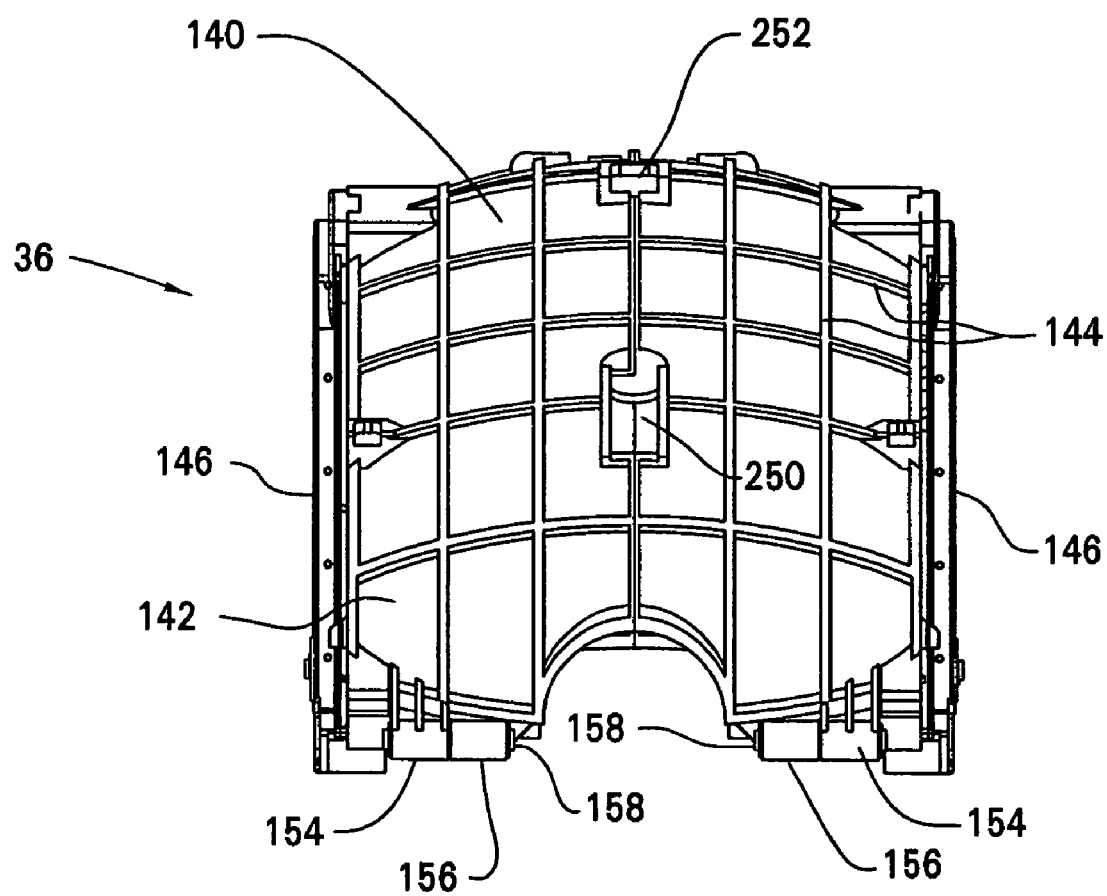
FIG. 8 is a view, looking upwardly of the static plate, the tubular sleeves of the dynamic plate also being visible.
Figure 9:
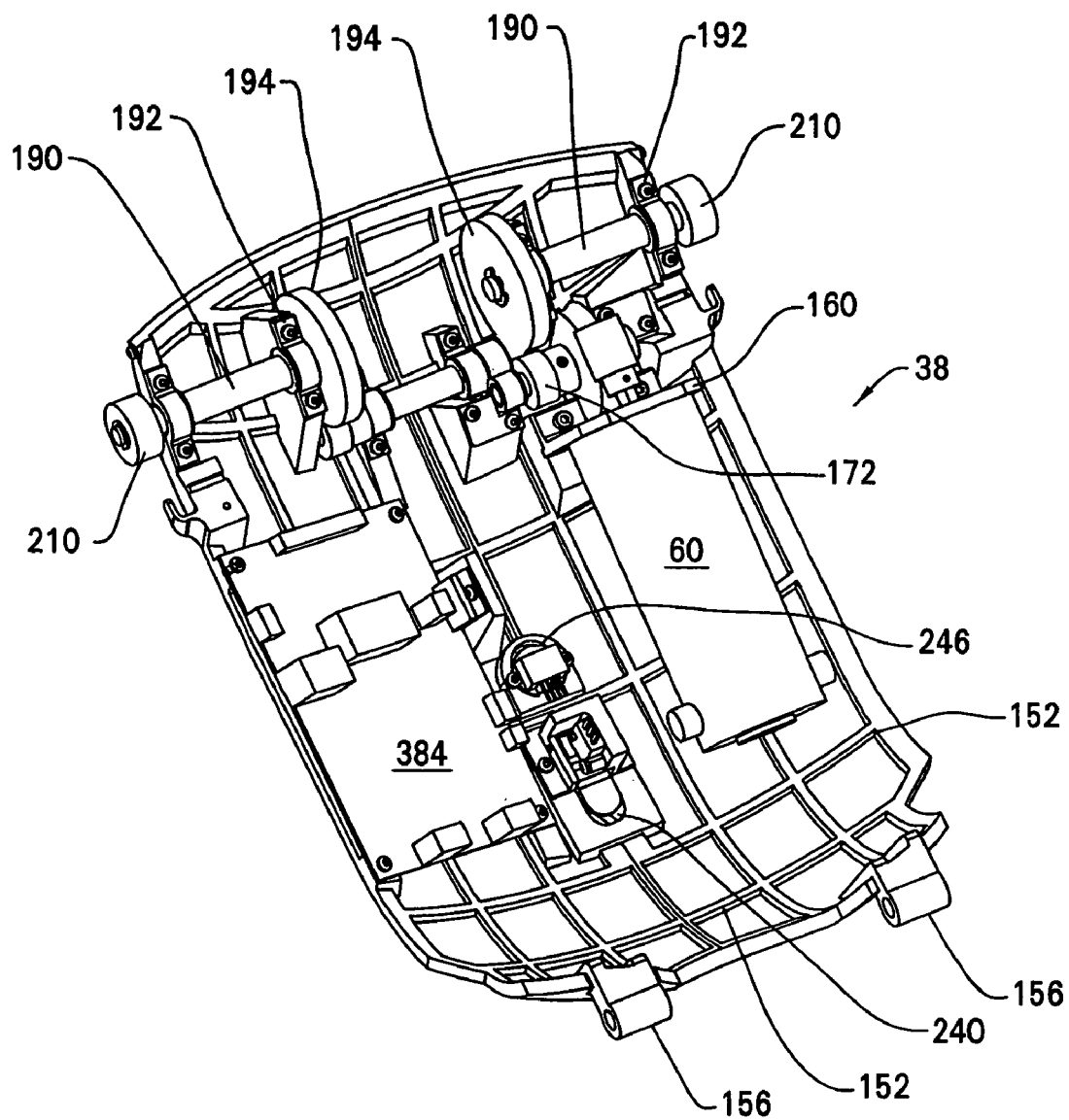
FIG. 9 is a perspective view of the components attached to the dynamic plate that actuate the dynamic plate.

Static plate 36, now described by reference to FIGS. 7-9, is an elongated structure that has top and bottom end portions 140 and 142, respectively, that are both curved rearwardly, towards the cabinet back piece 66. The center portion of the plate has a concavo-convex profile along the lateral axis of the plate. The outer face of the static plate 36, the face directed towards the cabinet front piece 64, is formed with reinforcing ribs 144. Reinforcing lips 146 extend along the lateral edges of the static plate. Two tabs 148 are located on adjacent sides of the plate top portion 140. Tabs 148 receive threaded fasteners (not illustrated) used to hold the static plate 36 to the cabinet front piece 64.

The dynamic plate 38 is formed to have an outer surface that generally conforms to the inner surface of the adjacent static plate 36. The dynamic plate 38 is, however, shorter in width than the static plate 36. Dynamic plate 38 is formed so that the outwardly facing surface, the surface that presses against bag 44 is smooth. The opposed rearward facing surface of the dynamic plate 38 is formed to have reinforcing ribs 152.

The bottom of the dynamic plate 38 is pivotally connected to the static plate 36. Specifically, the static and dynamic plates 36 and 38, respectively, are provided with coaxial tubular pairs of sleeves 154 and 156, respectively. Sleeves 154 and 156 are located along the bottom ends of the plates 36 and 38, respectively, and are oriented so as to extend laterally along the plate ends. Sleeves 154 are integrally formed with the static plate 36 so as to be located adjacent the side edges of the plate 36. Sleeves 156 are integrally formed with the dynamic plate 38 so as to be located inboard of the side edges of the plate 38 and abut the inner ends of the adjacent sleeves 154.

Pins 158 extend through the sleeves 154 and 156 so that the dynamic plate 38 is able to pivot around the static plate sleeves 154.

Figure 10:
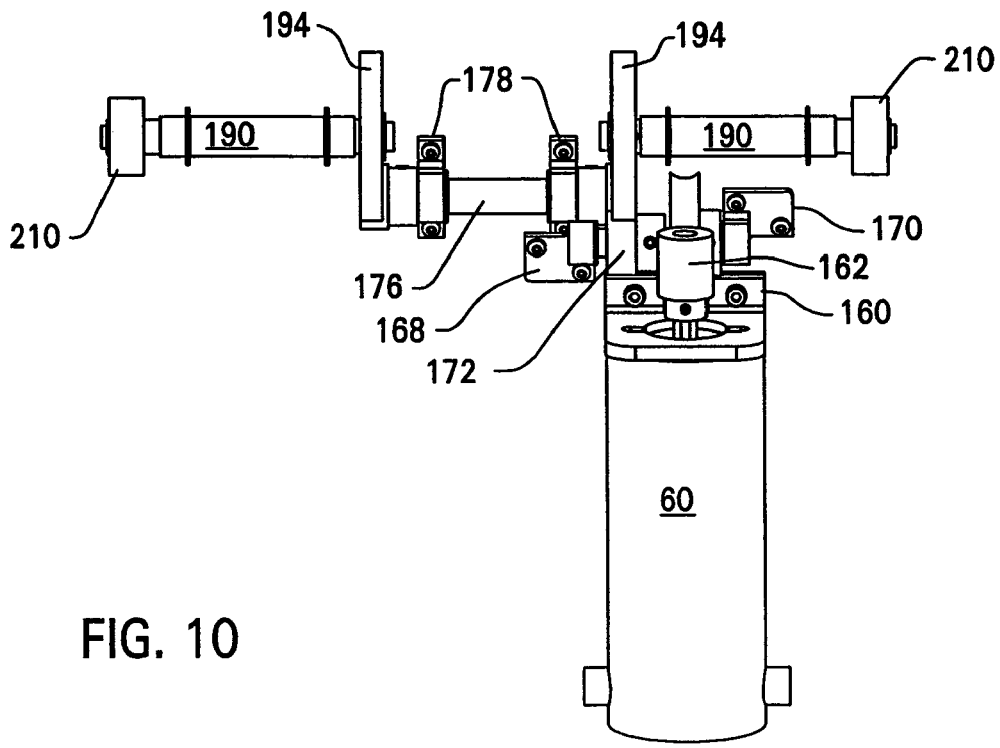
FIG. 10 is a back view of the pump motor and the drive train attached to the motor.
Figure 11:
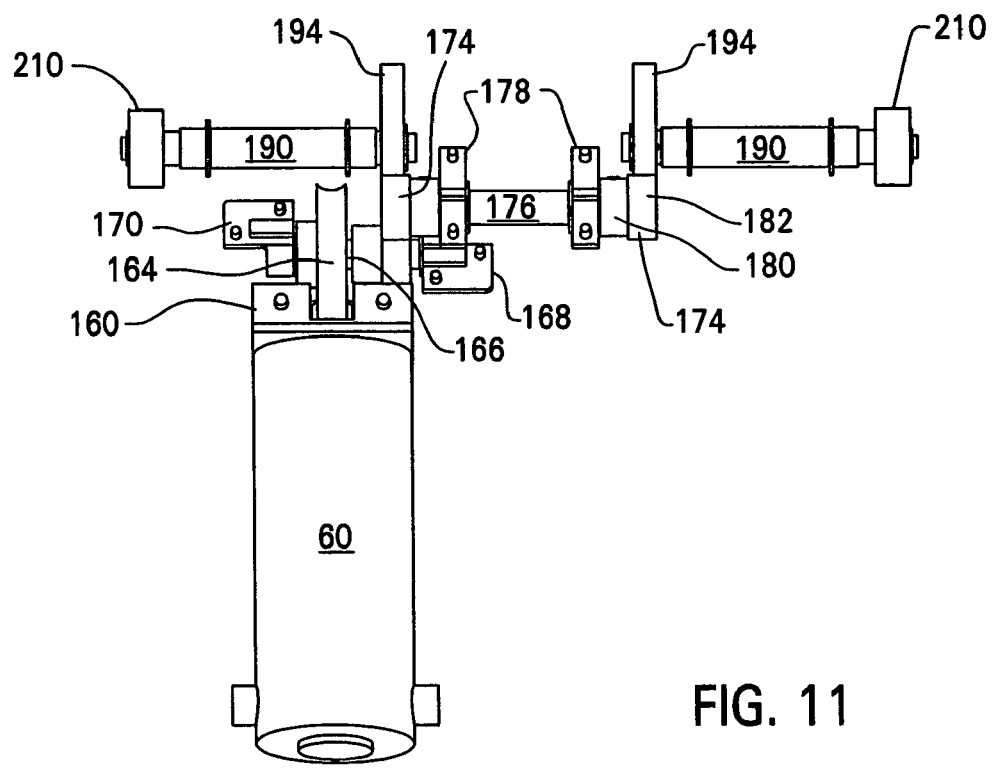
FIG. 11 is a front view of the pump motor and the drive train attached to the motor.

The position of the dynamic plate 38 relative to the static plate 36 is controlled by motor 60 and a rack-and-pinion assembly, seen by reference to FIGS. 9-11. More particularly, motor 60 is generally cylindrical in shape. One suitable motor that can be used as motor 60 is Model No. GM14904S011 manufactured by Pittman of Harleysville, Pa. Motor 60 is suspended from one side of the dynamic plate 38 by an L-shaped bracket 160 that extends outwardly from the rearwardly facing surface of the plate. More particularly, the outer surface of dynamic plate 38 is formed with a pylon (not identified) to which bracket 160 is attached. In the following description it should be understood that that other brackets secured to dynamic plate 38 are attached to similar pylons likewise integrally formed with the dynamic plate to extend rearwardly from the plate. To avoid redundancy, these pylons are not further discussed or identified.

The shaft of motor 60 drives a cylindrical worm gear 162. Worm gear 162 drives a receiving gear 164. The receiving gear 164 is attached to a horizontally extending receiving shaft 166 mounted to the dynamic plate 38. More particularly, brackets 168 and 170 rotatably hold the receiving shaft 166 to the dynamic plate 38. It should be understood that sleeve shaped bushings (not illustrated) of low friction solid material located between the shaft 166 and brackets 168 and 170 provide a low friction interface between the shaft and the static brackets. Similar bushings not discussed further perform similar functions with regard to the additional shafts that, as discussed below, are similarly mounted to the dynamic plate 38. Also not illustrated or otherwise further discussed are the fasteners, for example, threaded fasteners used to hold the brackets to the pylons to which the brackets are mounted.

A driving gear 172 is mounted to receiving shaft 166 to rotate in unison with the shaft. The driving gear 172 engages a spur gear 174 that is mounted to a spur shaft 176 also rotatably mounted to the dynamic plate 38. A pair of spaced apart brackets 178 rotatably hold spur shaft 176 to the rearwardly facing surface of dynamic plate 38. As seen by reference to FIG. 10, two spur gears 174 are mounted to spur shaft 176. Each spur gear 174 is attached to an end of the spur shaft 176. The spur shaft 176 is mounted to the dynamic plate 38 to extend perpendicularly across the longitudinal axis of the plate. Brackets 178 are positioned so that the ends of spur shaft 176 extend beyond the ends of the bracket. Each spur gear 174 has a reduced diameter neck 180 located adjacent bracket 178. Spur gear 174 has a head 182, integral with neck 180 that has a larger diameter than the neck and that forms the toothed portion of the gear.

While not illustrated, it should be understood that in some versions of the invention, it may be desirable to provide the brackets, such as brackets 168, 170 and 178, with alignment tabs. These tabs extend inwardly from the surfaces of the brackets with which they are integral and abut the adjacent dynamic plate pylons. The tabs seat in cutout notches formed in the pylons. The tabs assist in aligning the brackets, gears, and shafts by reducing tolerance stack-ups.

Also mounted to the dynamic plate 38 are two coaxially aligned drive shafts 190. Each drive shaft 190 is held in position by two spaced apart brackets 192. Attached to the inner end of each of drive shaft 190 is a receiving gear 194. Each receiving gear 194 engages an underlying one of the spur gears 174.

Figure 12:
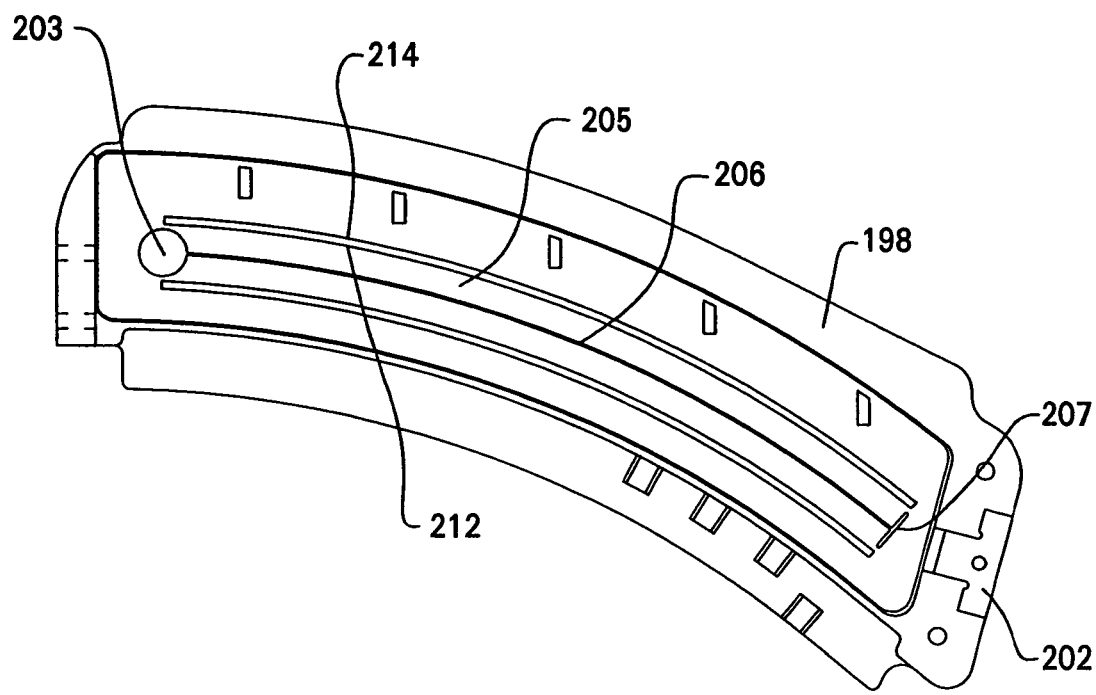
FIG. 12 is a side view of one of the arms that extend rearwardly from the static plate.
Figure 13:
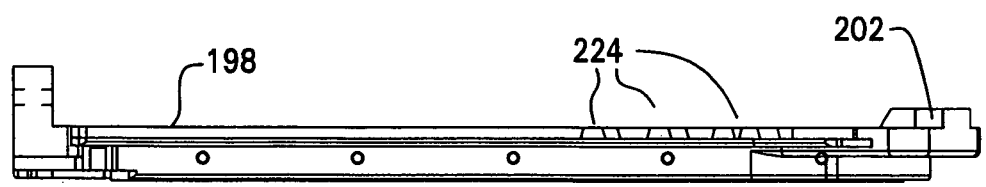
FIG. 13 is a bottom view of the arm.

From FIG. 7, it can be seen that the outer end of each drive shaft 190 extends beyond the adjacent side edge of the dynamic plate 38 through an elongated, curved slot 196 in an adjacent arm 198. The arms 198, seen best in FIGS. 12 and 13, are attached to the opposed sides of the static plate top end portion 140. More particularly, each arm 198 has a T-shaped boss 202 that is directed to the complementary static plate tab 148. Each plate boss 202 seats in a complementary shaped recess formed within the outer surface of the tab 148 (tab recesses not identified). This boss-in-recess arrangement inhibits movement of the arm 198 relative to the static plate 36.

An arcuately shaped guard strip 205, formed of a flexible material such as felt or rubber, is seated in each arm slot 196. The guard strips 205 function as barriers that prevent material placed in the center of the pump from finding its way into the space between the associated arm and the adjacent cabinet side panel 70. Each guard strip 205 is formed with an arcuate slit 206 that is centered along the curved longitudinal axis of the arm slot 196 in which the guard strip is seated. The slits 206 function as the openings through which the drive shafts 190 extend through the guard strips 205. A cross slit 207 extends laterally across the end of slit 206 proximal to the static plate. Slits 207 provide the opposed portions of the guard strips 205 flexibility. Each guard strip is provided with a circular opening 203 at the end of the slit 206 distal from the static plate 36. It is anticipated that, for a portion of the time, the drive shafts 190 will extend through the openings 203. Thus, by providing the guard strips 205 with the openings 203, the likelihood that the drive shafts 190 will, over time, permanently deform the guard strips is substantially reduced.

A pinion gear 210 is mounted to the end of each drive shaft 190 that extends through the associated arm slot 196 and guard strip 205. Each pinion gear 210 engages the teeth of a rack 212 mounted to the adjacent arm 198. More particularly, each rack 212 is mounted to a lip 214 integral with each arm 198 that extends perpendicularly from the top of each arm. Each rack 212 extends downwardly from the associated lip 214. The racks 212 have curved profiles similar to those of the arms 198 to which the racks are attached. The rotation of the pinion gears 210 relative to the racks 212 is what causes the dynamic plate 38 to extend and retract relative to the static plate 36.

Figure 14:
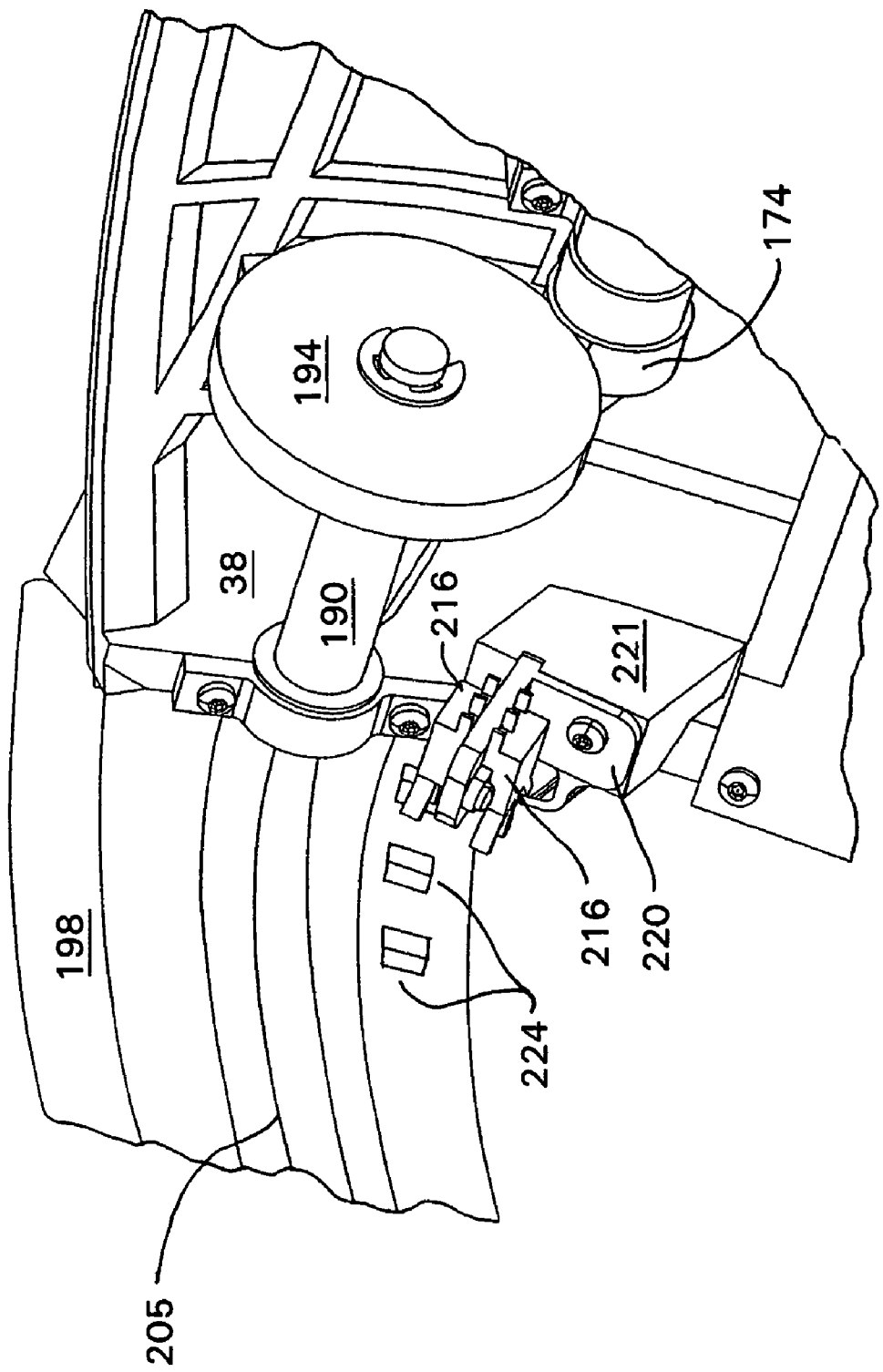
FIG. 14 depicts how the top of the static plate interfaces with an adjacent one of the arms.

Four microswitches 216, two of which are illustrated in FIG. 14, are mounted to the dynamic plate 38 and are positioned to abut against an adjacent arm 198. More specifically, an L-shaped bracket 220 is mounted to a pylon 221 integral with the dynamic plate 38 immediately below the outermost bracket 192 to which an adjacent drive shaft 190 is mounted. Two microswitches 216 are mounted to the opposed sides of the section of bracket 220 that extends away from the dynamic plate 38. While not shown, it should be understood that two identical microswitches 216 are mounted to an identical bracket 220 on the opposed side of the dynamic plate 38.

Each microswitch 216 has a follower 222 that is outwardly directed towards the adjacent arm 198. Arrays of spaced apart indicator bumps 224 are disposed on the surfaces of the arms 198. The indicator bumps 224 are each disposed within the arcuate path traveled by a separate one of the microswitch followers 222. As the dynamic plate 38 extends toward/retracts away from the static plate 36, each microswitch follower 222 pivots as a consequence of the follower traveling over the indicator bumps 224 that are complementary to the follower. The pivoting of the follower 222 causes the associated microswitch 216 to change state so as to provide a signal representative of the position of the microswitch and, therefore, the dynamic plate 38.

Collectively, the microswitches 216 provide signals representative of: when the dynamic plate is in the fully opened position to receive a 3 lt. bag; when the dynamic plate is in the partially opened position to receive a 1 lt. bag; when the dynamic plate is in the fully closed position; and when the dynamic plate is in a number of selected intermediate positions between the open and closed positions. A single microswitch 216 could be employed to provide the above information. The multiple microswitches 216 provide the pump 30 with overlapping data regarding the position of the dynamic plate 38. These data are useful in the event one microswitch fails to generate data that correctly identifies the position of the dynamic plate 38.

Figure 16:
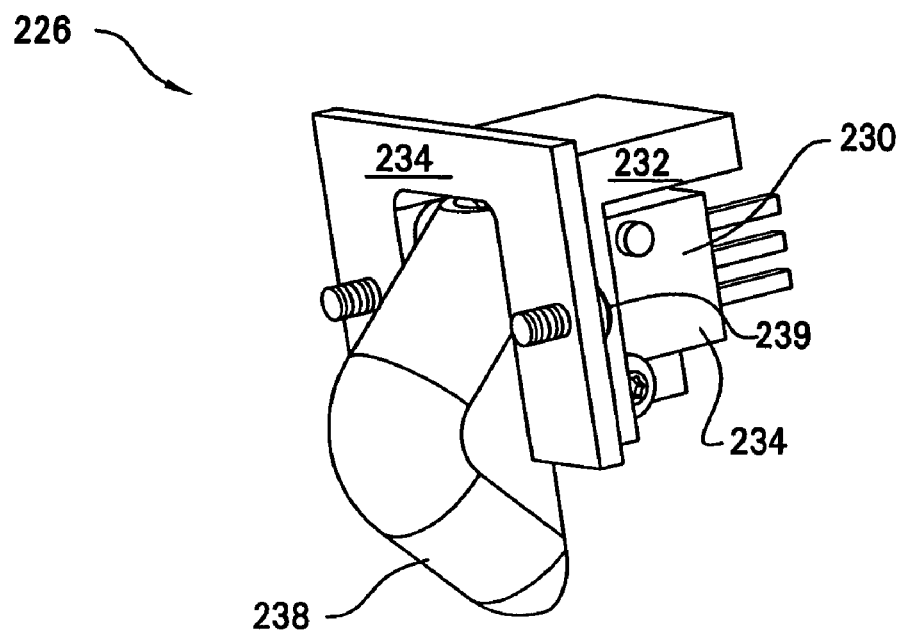
FIG. 16 is a perspective view of the bag presence sensor assembly.
Figure 15:
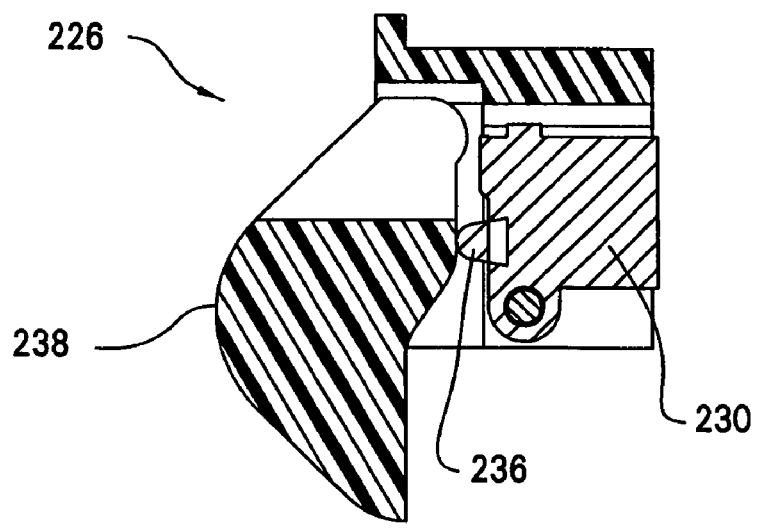
FIG. 15 is a cross sectional view of the bag presence sensor assembly.

There are two additional sensor elements attached to the dynamic plate 38, a bag presence sensor 226 and a bag pressure sensor 228. Referring now to FIGS. 15 and 16, it can be seen that the bag presence sensor 226 includes a microswitch 230. Microswitch 230 is seated in a mounting fixture 232 that has a top panel and opposed side panels that surround the adjacent surfaces of the microswitch, (fixture top and side panels not identified). Mounting fixture 232 also has a frame 234 with an inverted-U-shape that forms the front of the fixture.

Microswitch 230 has a plunger 236 that extends forward of the body of the microswitch. A triangularly shaped sensor head 238 is pivotally attached to the mounting fixture 232 forward of the microswitch 230. Specifically, the sensor head 238 is mounted to the mounting fixture so that a surface of the base of the head normally abuts the microswitch plunger 236.

The mounting fixture frame 234 is the portion of the bag presence sensor 226 that is physically secured to the dynamic plate 38. Threaded fasteners 239 secure the mounting fixture frame 234 to the adjacent sections of the dynamic plate 38.

The dynamic plate 38 is formed to have an oval shaped opening 240 (FIG. 9). When the pressure sensor 226 is mounted to the dynamic plate 38, sensor head 238 is seated in opening 240 and extends through the opening into the bag well 40.

Figure 17:
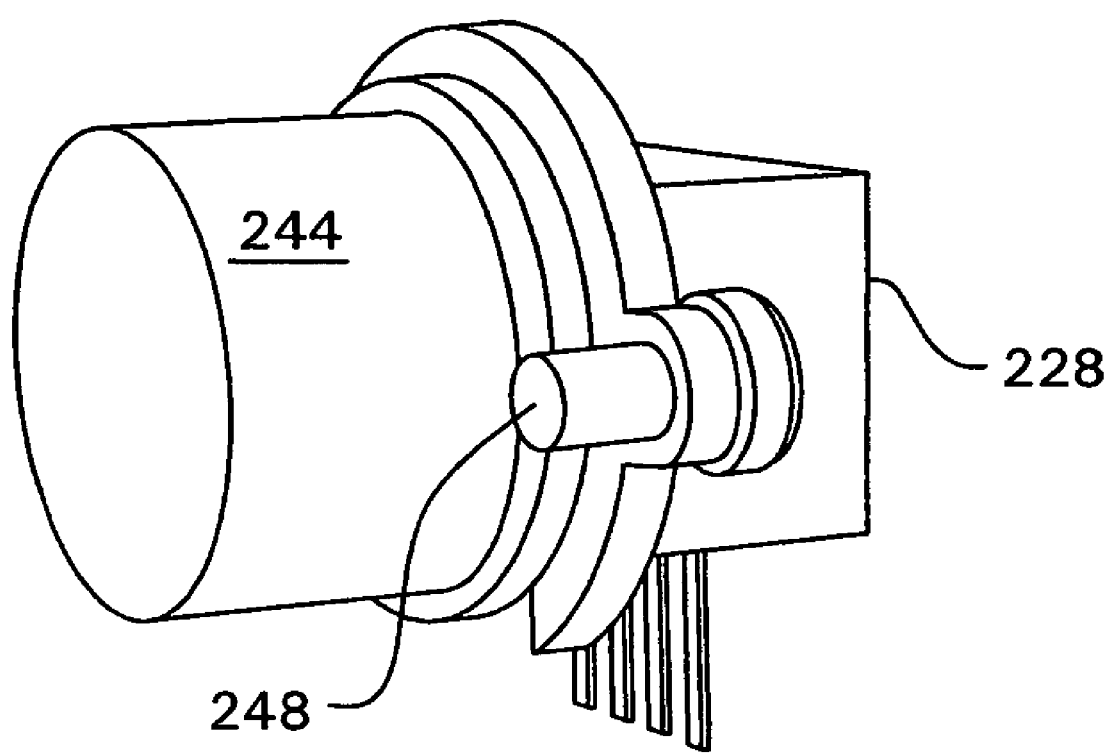
FIG. 17 is a perspective view of the bag pressure sensor assembly.

The bag pressure sensor 228 is any convenient force sensitive transducer. As seen in FIG. 17, a cylindrically shaped button 244 is secured over the pressure sensitive face of sensor 228. Bag pressure sensor 228 is mounted to dynamic plate 38 so that button 244 extends through a complementary opening 246 (FIG. 9) formed in the plate. Threaded fasteners 248 (one shown) secure the bag pressure sensor 228 to the dynamic plate 38.

Returning to FIGS. 7 and 8, it can be seen that the static plate 36 is formed with openings 250 and 252 that are centered on the longitudinal axis of the plate. Opening 250 is oval in shape and is positioned to receive head 238 of the bag presence sensor 226. Opening 252 is round in shape and is positioned to receive button 244 of the bag pressure sensor 228. Openings 250 and 252 receive, respectively, the sensor head 238 and button 244, as well as the overlying portion of the empty bag 44, when the dynamic plate 38 moves to the closed position relative to the static plate 36.

Figure 18:
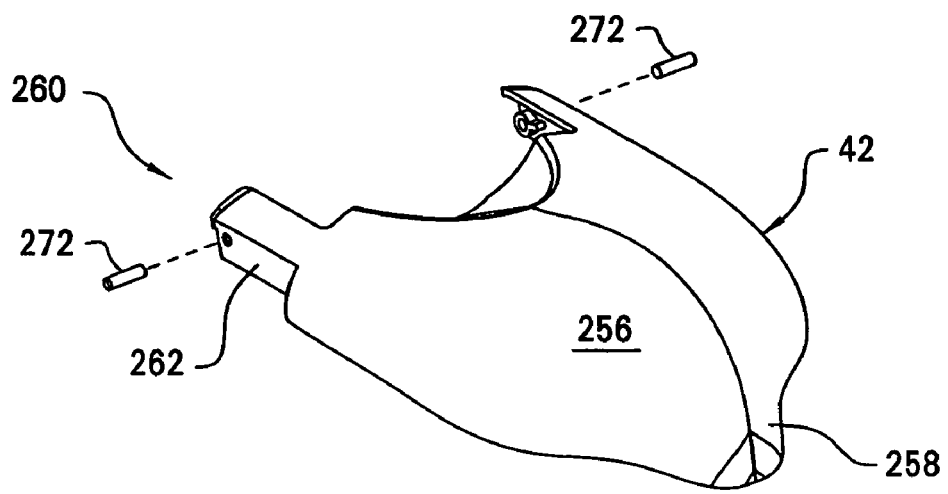
FIG. 18 is a perspective view of the lid.
Figure 19:
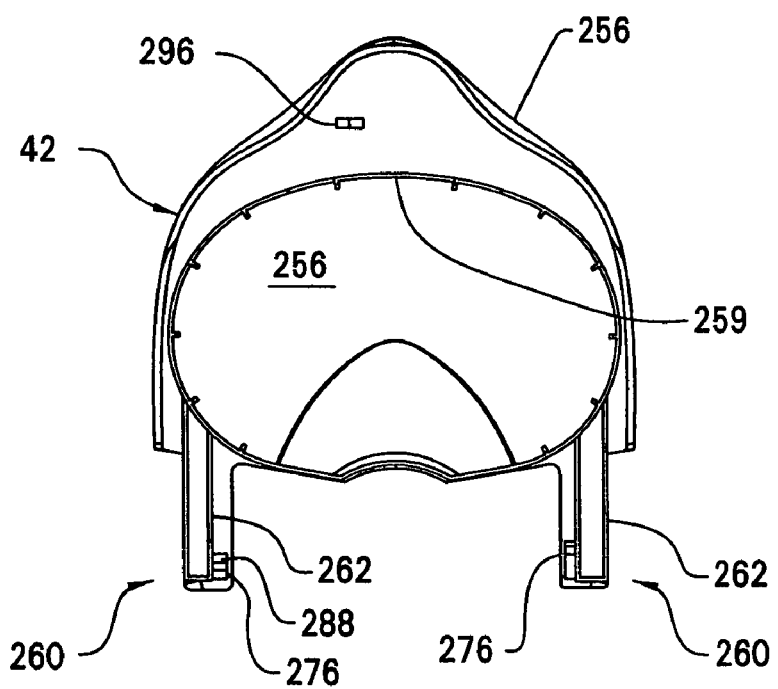
FIG. 19 is a bottom view of the lid.

As seen best in FIGS. 18 and 19, lid 42 has a main body 256 that covers the opening in the cabinet 32 defined by rim 74 and the portion of the cabinet top panel 72 that defines the rim. Lid 42 is further formed to have a nose 258 that extends a small distance forward of the main body 256. When the lid 42 is closed, the nose 258 extends over the spike spout 52 and the end of the tube set 46 connected to the spike 48. Lid main body 256 is formed to have a closed reinforced web 259 that extends downwardly from the inner surface of the main body. When the lid 42 is closed over the opening in the cabinet 32, web 259 is in close proximity to, and extends a slight distance below, cabinet rim 74. The web 259 thus functions as a splash guard to prevent stray liquid in the cabinet 32 from being discharged.

Two spaced apart parallel legs 260 extend rearwardly from the lid main body 256 so as to connect the lid 42 to the cabinet top panel 72. Each leg 260 is flat and is generally a coplanar extension of the lid main body. A three-sided, U-shaped web 262 extends downwardly from the bottom surface of each leg to provide the leg with structural strength. The opposed ends of each web 262 abut the main body web 259.

The free end of each leg 260 is pivotally attached to a complementary mounting pylon 264 that are secured to the cabinet top panel 72 and now described by reference to FIGS. 20 and 21. Each pylon 264 has a sleeve 266. The sleeves 266 receive threaded fasteners (not illustrated) that extend upwardly, out of the cabinet top panel 72 so as to hold the pylons 264 to the cabinet 32. Each pylon 264 is generally U-shaped so as to form a closed-end channel 268. Channels 268 function as spaces for receiving the lid legs 260 and associated webs 262.

A pivot pin 272 pivotally connects each lid leg 260 to the associated mounting pylon 264. Each pivot pin 272 seats in a pair of opposed openings in the 253 and 254 formed in the facing walls of the pylon 264 that define channel 268. Also seen is that one side wall is formed with a reinforcing step 255 adjacent the associated opening 254. The opposed outer surface of the pylon 264 is formed with an indentation 257 through which the pin 272 is inserted in opening 254. The pivot pin 272 also extends through a sleeve 276 integral with the inner face of the inwardly located section of the leg web 262.

A torsion spring (not illustrated) is wrapped around each pivot pin 272. One leg of each torsion spring bears against the portion of the cabinet top panel 72 below channel 268. The opposed leg of the torsion spring bears against the overlying inwardly directed face of the associated lid leg 260. The torsion springs thus supply a biasing force to urge the lid 72 upwardly when the lid is not otherwise latched.

Figure 20:
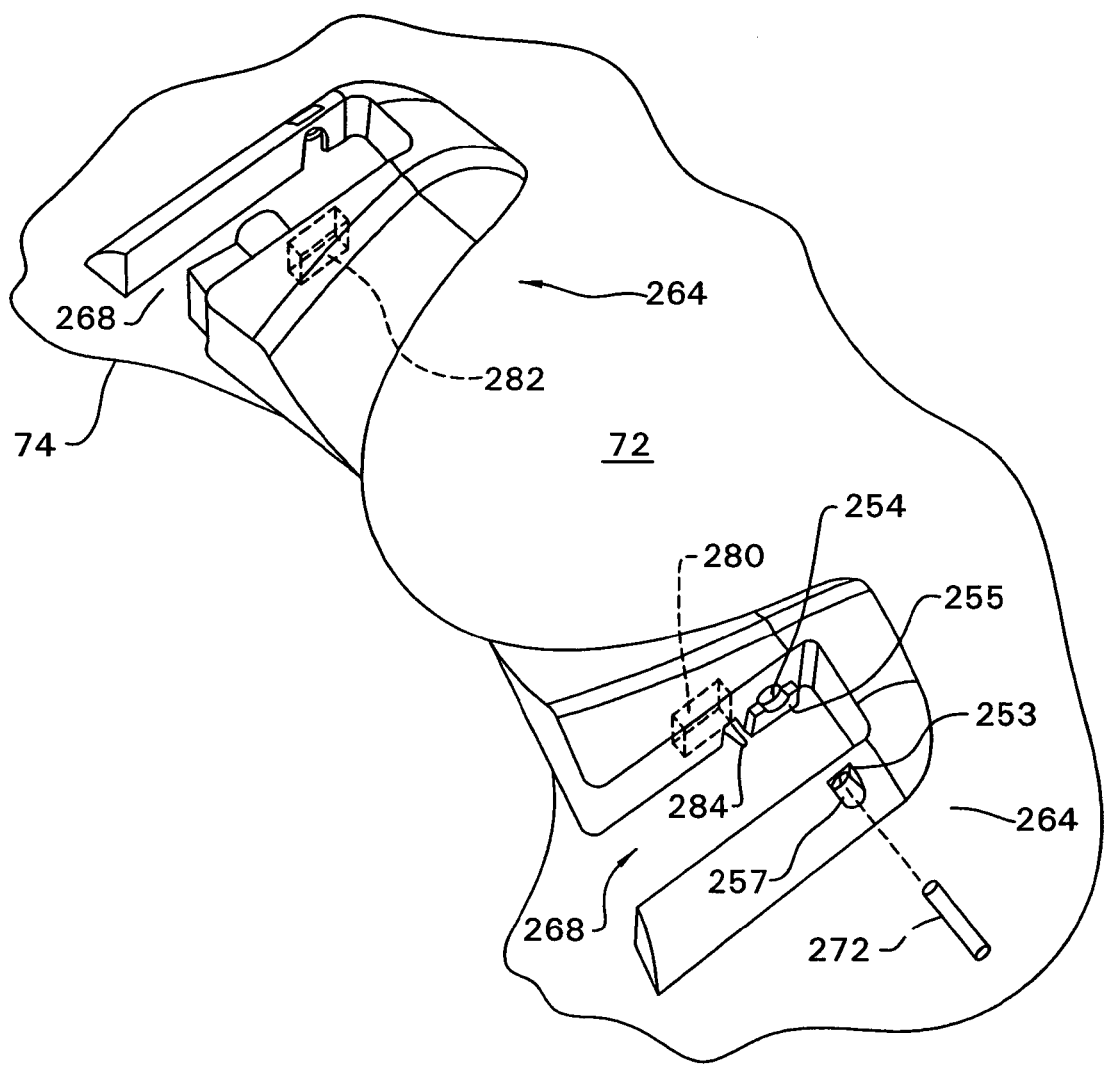
FIG. 20 is a top view of the portion of the cabinet to which the lid is mounted.
Figure 21:
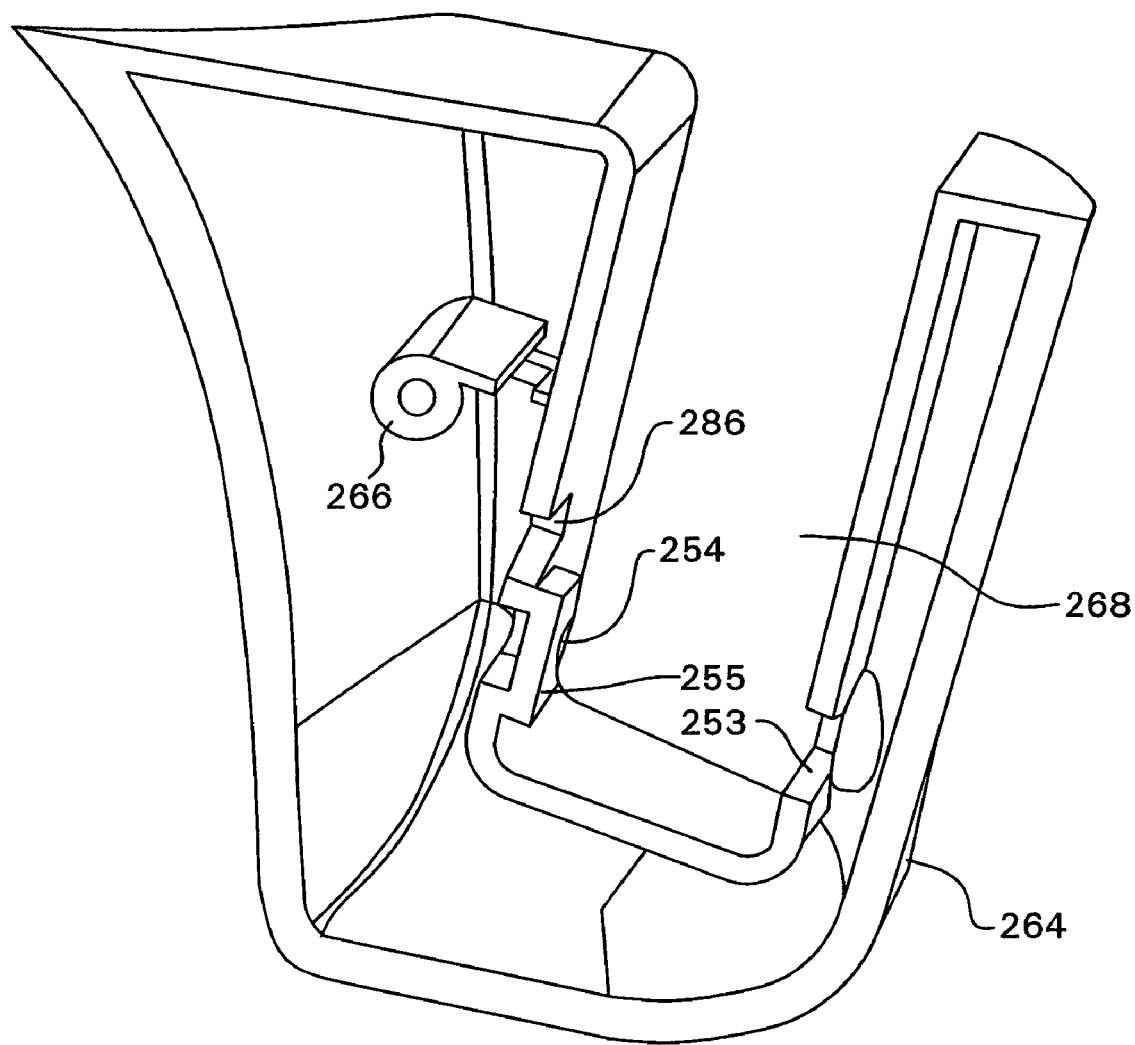
FIG. 21 is a bottom view of one of the mounting pylons to which the lid is mounted.

Two microswitches 280 and 282, shown in phantom in FIG. 20, are disposed in the mounting pylons 264 to provide signals indicating the open/closed state of lid 42. One switch 280 or 282 is disposed in each pylon 264. Each switch has a follower 284 that extends into the associated pylon channel 268. The followers 284 extend through openings 286 formed in the walls of the pylons that define channels 268. A small tab 288 is formed integrally with each leg sleeve 276 so as to extend forward from the sleeve.

The microswitch followers 284 are normally biased to extend horizontally into the associated pylon channel 268. When the lid 42 is closed, tabs 288 press against the followers 284 to urge the followers diagonally downwardly. This displacement of followers 284 causes the associated microswitches 280 and 282 to undergo a state change. As will be discussed hereinafter, microswitch 280 is actuated to provide a POWER_ON signal used to actuate pump 30. Microswitch 282 is actuated to provide an indication of the lid open/closed state.

Figure 23:
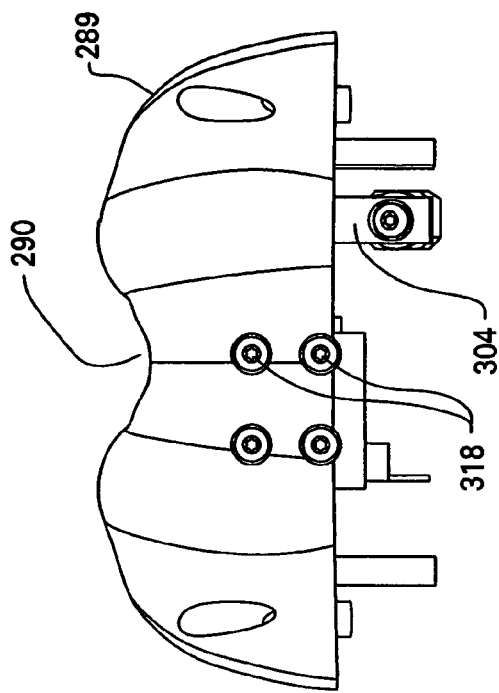
FIG. 23 is a back view of the pump spout.
Figure 22:
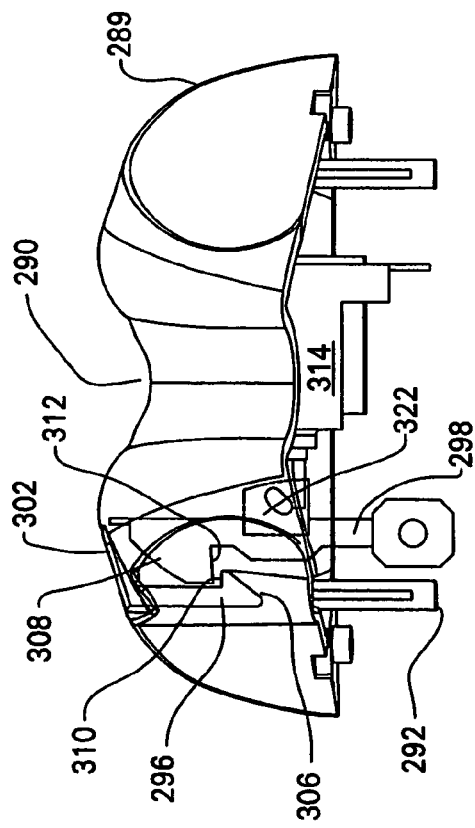
FIG. 22 is a front view of the pump spout.
Figure 24:
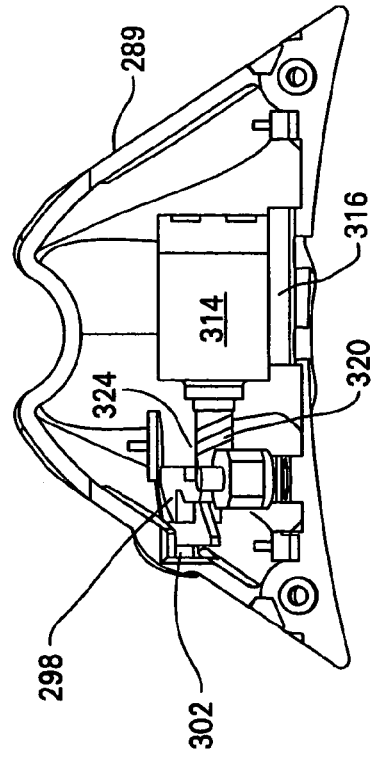
FIG. 24 is a bottom view into the pump spout.

The lid 42, when closed, releasably latches into a pump spout 289, now described by reference to FIGS. 22-24. The spout 289 is generally in the form of a half-clam shell member that generally has a triangularly shaped profile. Spout 289 is further formed to have inwardly curved center section 290 that extends from the proximal back end of the spout to the front distal end. The spout center section 290 thus defines a space immediately above the spout 289, and below the lid 42, in which the proximal end of the outflow tube 50 and spike spout 52 are located.

Pump spout 289 is further formed to have parallel opposed downwardly directed fingers 292. Fingers 292 seat in concealed slots formed in complementary fingers in the cabinet front piece 64 below rim 74 (cabinet fingers and slots not shown). Threaded fasteners (not shown) extend through sleeves 294 formed internally to the spout 289 and engage in complementary bores in the front piece 64 so as to secure the spout to the cabinet 32.

The lid 42 has a hook 296 that engages a latch 298 that is pivotally attached to the spout 289. As seen in FIG. 19, hook 296 extends downwardly from an inner surface of the lid nose 258. The hook 296 extends into an opening 302 formed in the top of the spout 289. Latch 298 is pivotally attached at one end to a finger 304 that extends downwardly from the spout.

The hook and latch 296 and 298, respectively, are formed with opposed angled surfaces 306 and 308, respectively that abut when the lid 42 is closed. As a consequence of hook surface 306 abutting latch surface 308, the latch 298 pivots away from the hook 296. Hook and latch 296 and 298, respectively, are further formed with horizontal surfaces 310 and 312, respectively that extend away from the ends of surfaces 306 and 308, respectively. Once the lid 42 is pushed downwardly to the extent that hook surface 306 and latch surface 308 no longer abut, latch surface 312 engages over hook surface 310 to hold the hook 296 and, by extension, lid 42 to the spout 289.

The pivotal position of latch 298 is controlled by solenoid 314, also attached to spout 289. The solenoid 314 is mounted to a plate 316 internal to and formed integrally with the spout 289 by fasteners 318. Solenoid 314 has a retractable plunger 320 that is attached to tab 322 integral with the latch 298. A coil spring 324 disposed around the plunger 320 extends between the shell of the solenoid 314 and the latch 298.

Spring 324 exerts an outward force on the latch to normally bias the latch 298 away from the solenoid 314. The spring 324 thus provides the force required to pivot the latch 298 into the locked position wherein latch surface 312 engages over hook surface 310.

Figure 25:
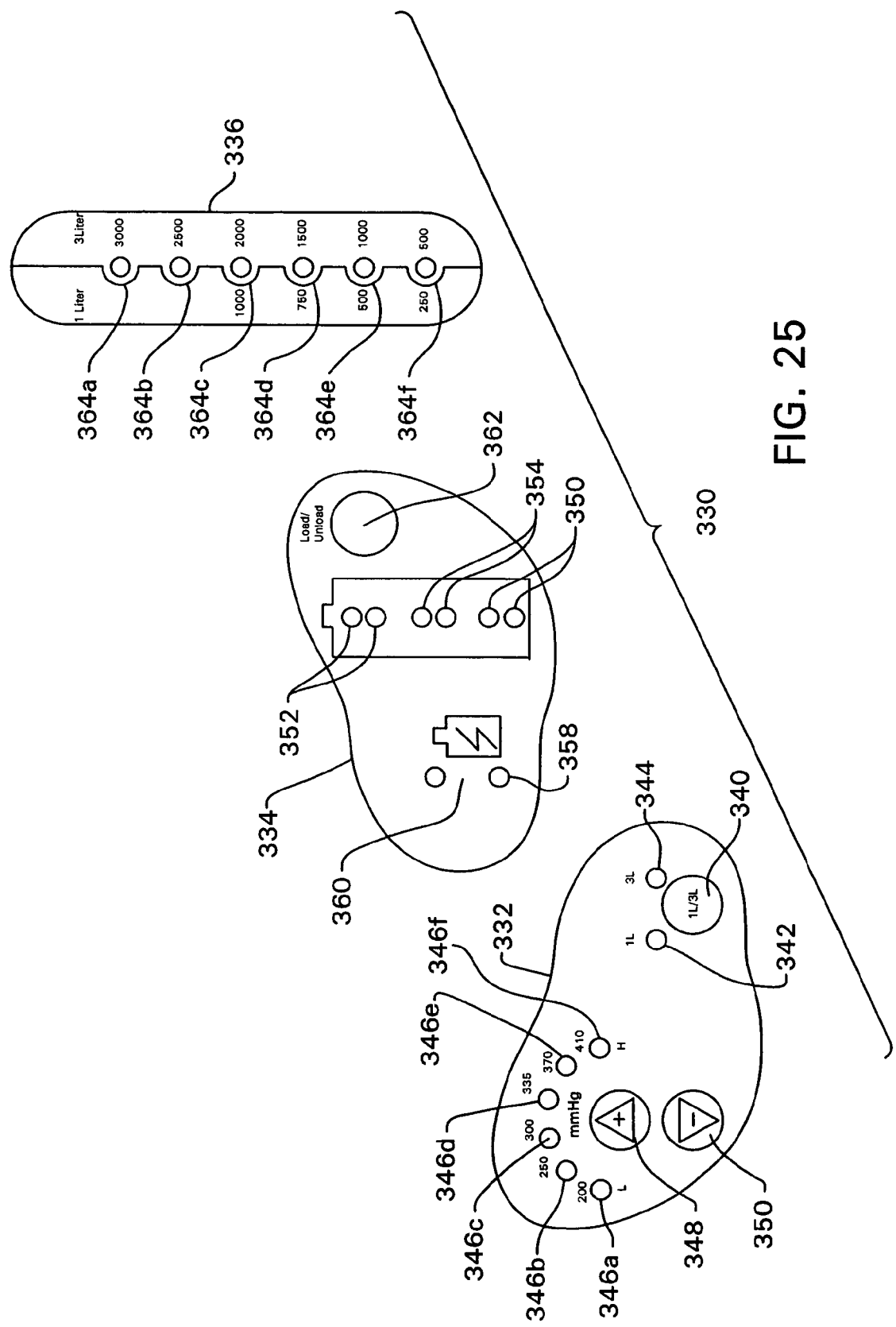
FIG. 25 depicts the user interface panels of the pump.

FIG. 25 illustrates the components of the user interface 330 of the pump 30 of this invention. Interface 330 includes a number of LEDs that provide information about the operation state of the pump 30 and a number of switches that control the operation of the pump. The LEDs are mounted to the cabinet front panel 68 and are encased in four separate membranes 332, 334, and two membranes 336. The switches are membrane switches, contained within two of the membranes, membranes 332 and 334.

Specifically, membrane 332 is mounted to the curved edge surface between the front and top panels 68 and 72, respectively, of the cabinet 32 adjacent one side of opening 74. Membrane 332 forms part of a first switch, switch 340. The user presses switch 340 to indicate if a 1 lt. or 3 lt. bag 44 is to be used with the pump. Immediately above switch 340 are two LEDs 342 and 344 that are selectively actuated to indicate the size of the bag 44 for which the pump is presently configured. LED 342 is illuminated when the pump is configured for use with a 1 lt. bag; LED 344 is illuminated when the pump is configured for use with a 3 lt. bag.

To the left and above switch 340, membrane 332 shields a circular set of LEDs 346a, b, c, d, e and f. One of LEDs 346a, b, c, d, e or f is individually illuminated to indicate the pressure at which the irrigation solution should be discharged from the pump 30 when the pump is so actuated. The user sets the pressure by selectively depressing one of two membrane switches 348 and 350 also part of membrane 332. Switch 348 is pressed to raise the pressure of the discharge flow; switch 350 is pressed to lower the pressure of the discharge flow.

Membrane 334 shields a number of LEDs that provide information regarding the charging of the batteries 132 internal to the pump. Three pairs of LEDs 352, 354 and 356 provide information regarding the charge state of the batteries. LEDs 352, which emit green light, are actuated when the batteries 132 is essentially fully charged. LEDs 354, which emit amber light, are actuated when the batteries 132 are partially charged yet still able to provide the power required to fully actuate the motor 60. LEDs 356 emit red light and are actuated when the battery strength signal indicates that the batteries 132 only have a small amount of charge to actuate the motor 60.

Membrane 334 also shields LEDs 358 and 360 that provide information regarding the charging of the batteries 132. While the power supply 130 is charging the batteries, LED 358 is actuated. Once the power supply 130 completes the charging of the batteries 132, LED 360 is actuated. In preferred versions of the invention, LEDs 358 and 360 emit, respectively, amber and green light.

The remaining membrane switch, switch 362 is integral with membrane 334. Membrane switch 362 is depressed in order to remove the bag 44 mounted to the pump and load a new bag.

Membranes 336 and 338 are mounted to the opposed side edges adjacent the cabinet top panel 72. Each membrane 336 includes a set of LEDs 364a, b, c, d, e and f. When a bag 44 is disposed in the well 40, one of the LEDs 364a, b, c, d, e or f is illuminated to provide an indication of the amount of fluid that remains in the bag.

Figure 27:
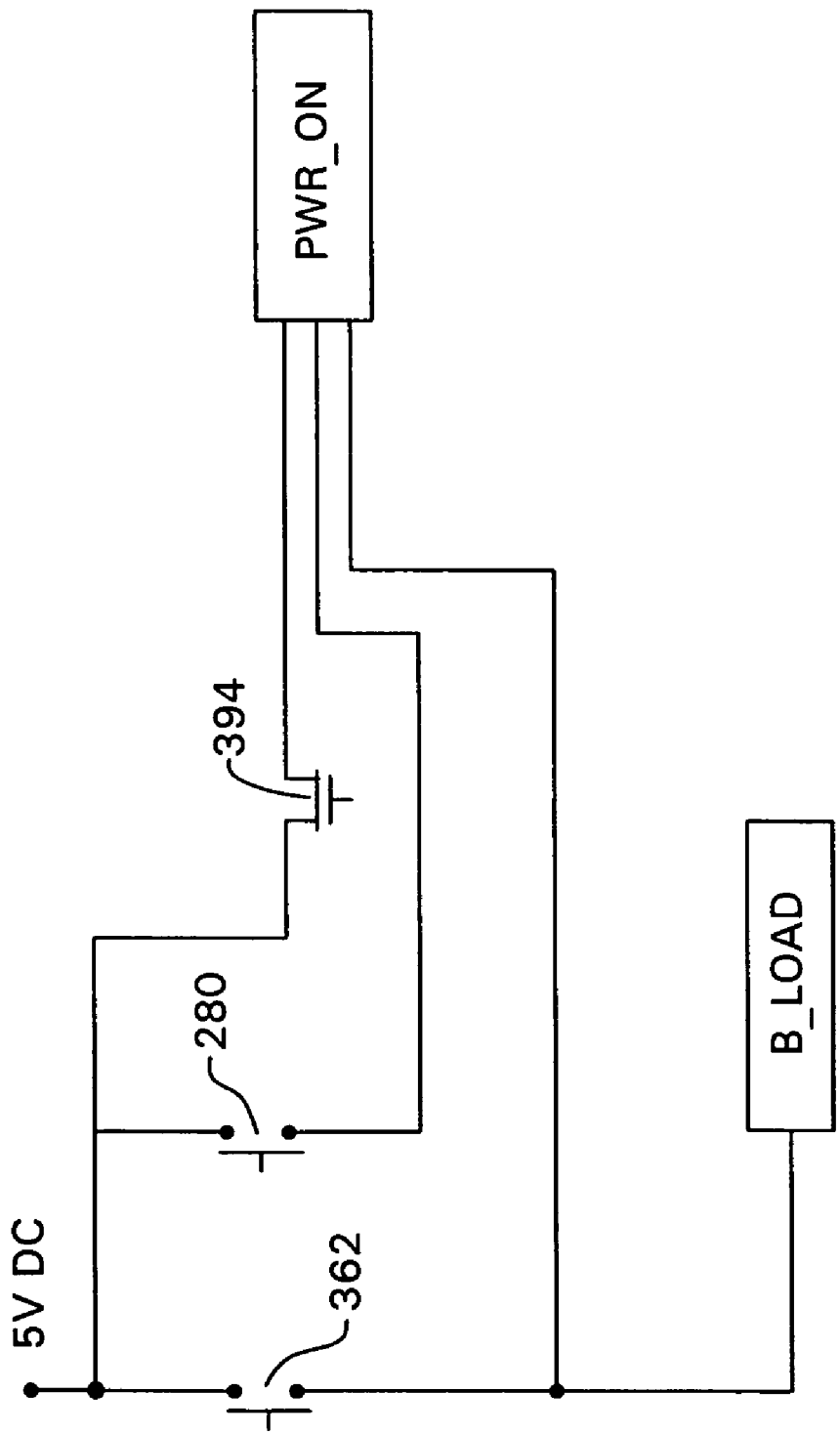
FIG. 27 is a schematic diagram illustrating the components that apply the POWER_ON signal to the main controller.
Figure 28:
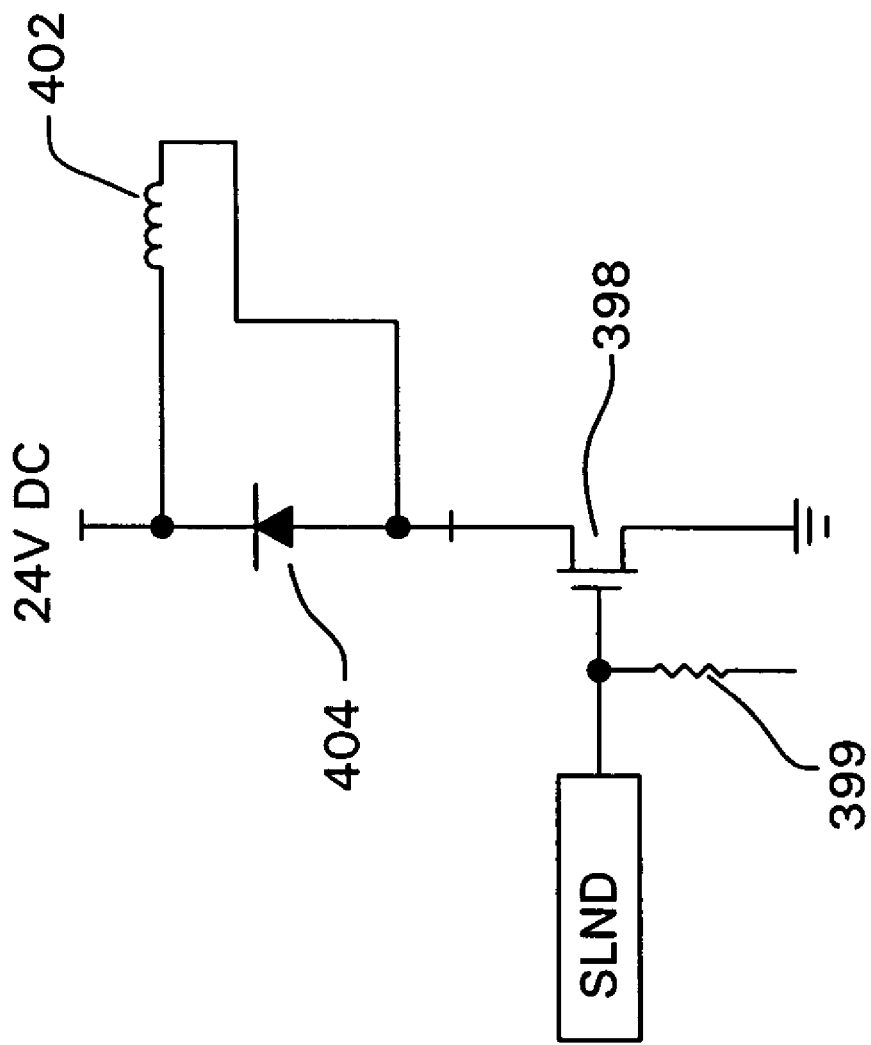
FIG. 28 is a schematic diagram of the components that energize the solenoid.

FIGS. 26-28 illustrate the electrical components integral with pump 30 that actuate the pump. Briefly, the pump includes the rechargeable batteries 132 that provide the power used to actuate the motor 60. Power supply 130 both charges the batteries 132 and provides information regarding the charge state of the batteries. A main controller 380 regulates the actuation of the motor 60 based on commands entered by the user. Main controller 380 also actuates the LEDs integral with the user interface 330 to provide information about the state of the pump 30.

A motor controller 382, in response to control signals from the main controller 380, regulates the application of power from batteries 132 to the windings of motor 60 so as actually cause the appropriate actuation of the motor.

Main controller 380, motor controller 382 and many of the other electrical components integral with pump 30 are mounted on a printed circuit board 384. The printed circuit board 384 is attached to the inner surface of the dynamic plate 38, on the side opposite the side on which the pump is located (FIG. 9).

Power supply 130 is any suitable charging assembly for converting a line AC signal into a DC signal suitable for charging batteries 132. While the individual components are not shown, it should be understood that power supply 130 includes a step down transformer for converting the line voltage to a lower AC voltage level. There is also an AC to DC rectifier and a filter to remove AC ripple wave from the output DC signal that is supplied to the battery. The AC for charging the battery comes from cord 386 connected to socket 128. When the batteries 132 are not being charged, the cord 386 is held to cabinet 32 by a strap (not illustrated).

Also internal to the power supply 130 is a battery charger 388 that regulates the application of current to the batteries 132 and provides data regarding the charge state of the batteries. One suitable battery charger 388 that can be employed with the pump of this invention is the LTC4008EGN manufactured by Linear Technology. A resistor 390 extends from the positive terminal of the batteries 132 to ground. The voltage across resistor 390 is provided to the battery charger 388.

The battery charger 388, based on whether or not current is being applied to the batteries 132, and the voltage across the batteries, asserts signals representative of the charging state of the battery charger. A first signal is asserted when the battery charger is actually in the process of charging the batteries 132. This signal is used to actuate LED 358. Once the power supply-battery charger sub assembly completes the charging of the batteries 132, the first signal is negated and a second signal is asserted. The second signal actuates LED 360.

The electrical circuit of the pump 30 of this invention also has a DC-to-DC converter, depicted in FIG. 26 as a 5 VDC regulator 392. This converter 392 steps down the signal from the batteries 132 and converts it into a 5 VDC signal. This 5 VDC signal is applied to a bus (not illustrated) from which it is available for use by the other components of the pump 30.

Main controller 380 is typically a microcontroller. One microcontroller that can be employed as a main controller 380 is the PIC16F874A manufactured by Microchip. The main controller 380 receives a number of input signals based on the actuation of the user depressed switches and the sensors that monitor the operating state of the components of the pump 30.

One of the input signals received by the main controller 380 is a basic 5 VDC POWER_ON (PWR_ON) signal that energizes the main controller 380. The initial application of the POWER_ON signal results in the main controller initiating a power up sequence internal to the main controller. As seen by reference to FIG. 27, the POWER_ON signal is initially applied to the main controller 380 as a result of one of either one of two events occurring. First, the depression of the bag load switch 362, the closing of the switch, results in the 5

VDC signal from voltage regulator 392 being applied to the pin of the main controller 380 to which the energization signal is applied. Alternatively, the closing of the lid 42 results in the closing of switch 280. The closing of switch 280 likewise ties the 5 VDC signal from voltage regulator 392 to the main controller 380 as a POWER_ON energization signal.

It will be further noted that the 5 VDC signal required to energize the main controller can also be applied to the main controller through a normally off n-channel FET 394. As part of the power on sequence, the main controller 380 turns on FET 394 (main controller to FET gate connection not shown) so the controller receives power through the FET 394. Since the power is now supplied to the main controller 380 through FET 394, the effect the open/closed states of switches 280 and 362 have on the application of the POWER_ON signal to the main controller is eliminated.

As part of the process of powering down the pump, main controller 380 turns off FET 394. This negates the application of the POWER_ON signal to main controller 380.

Another signal received by the main controller 380 is a BAG_LOAD (B_LOAD) signal. This signal is received by the user depressing the normally open switch 362 after the pump 30 is actuated. The depression of switch 362 results in a 5 VDC pulse signal being sent to the main controller as the BAG_LOAD signal.

Main controller 380 also receives, as a result of the depression of switch 340, a single pulse 1L/3L signal. Main controller 380, in response to receipt of the 1L/3L toggles the pump between the condition in which it is configured to accept a 1 lt. bag 44 of solution or a 3 lt. bag. Internal to the main controller 380 is a small electronically erasable memory, (not illustrated). The main controller 380 stores in this memory data indicating whether or not the pump is configured for operation with a 1 lt. bag or a 3 lt. bag. The assertion of the 1L/3L signal causes the main controller 380 to reset the pump to the bag size for which it presently is not configured. Depending on which bag size the pump 30 is presently configured to operate, the main controller selectively energizes LED 342 or LED 344.

The remaining user-generated signals main controller 380 receives are FLOW_RATE (F_R) signals. The FLOW_RATE signals, which are in pulse form, are generated as a consequence of the user depressing either switch 348 or switch 350. Internal to the erasable memory of the main controller 380 are data indicating the last user-selected flow rate for fluid from the pump 30. The depression of switch 348 results in a FLOW_RATE signal being sent to the main controller 380 that causes the controller to step up the selected flow rate. The depression of switch 350 results in a FLOW_RATE signal being sent to the main controller 380 which causes the controller to step up the selected flow rate. The selected flow rate is further stored in the main controller erasable memory. Main controller 380 also selectively actuates one of LEDs 346a, b, c, d, e or f to indicate the present pressure setting for the flow rate out of the pump 30.

Not shown, but understood to be present are debounce circuits associated with each user set switch 348, 350, 362. The debounce circuits associate that the signals generated as a result of the depression of these switch are of an appropriate length to be detectable by the main controller 380.

The main controller 380 also receives as input a bistate BAG_YES (BAG_Y) signal from microswitch 230. An analog BAG_PRESS (BAG_P) signal representative of the pressure of bag 44 is received from the bag pressure sensor 228. Main controller 380 receives from microswitch 282 a LID_ CLOSED (LID_C) signal representative of the open/closed state of the lid 42.

Main controller 380 also receives from microswitches 216 bistate PLATE_POSITION (P_P) signals. Microswitches 216 generate the PLATE_POSITION signals as a consequence of each microswitch follower 222 abutting one of the bumps 224 associated with the follower.

In response to the various input signals, main controller 380 generates a number of output signals. The primary output signals the main controller 380 generates are a set of motor control signals to the motor controller 382. The motor controller 382, based on motor control signals, selectively ties the winding of the motor 60 across batteries 132. One control chip that is suitable for the motor controller 132 of this invention is the L6203 manufactured by ST Microelectronics. Motor controller 382 is capable of applying the energization signal to the windings of motor 60 so that the motor 60 can be driven in both the forward and reverse directions. Motor controller 382 is further capable of establishing the speed of motor 60. This is accomplished by regulating the frequency with which the low side end of the winding, the end of the winding opposite the end to which the 24 VDC signal is applied, is tied to ground.

Main controller 380 also regulates the actuation of solenoid 314 by selectively generating a signal (SLND). As seen by reference to FIG. 28, in some versions of the invention, the SLND signal is applied to the gate of an n-channel FET 398. A resistor 399 is tied between the gate and ground. The drain and source of the FET 398 are, respectively, tied between the 24 VDC battery voltage bus and ground. The opposed ends of a winding 402 are tied to the line to which the 24 VDC signal is applied to the FET 398. A reverse biased diode 404 is disposed in the line leading to the FET drain so as to be between the lines leading to the solenoid winding 406. Thus, the assertion of SLND results in current flow through the FET 398. This current flows through the solenoid winding 406 so as to cause the retraction of latch 298.

The battery charger 388 also sends a signal to main controller 380 indicating the charge state of the batteries 132. Based on this signal, main controller 380 selectively actuates the appropriate pair of LEDs, 352, 354 or 356 that are part of user interface 330.

In some versions of the invention, when the battery strength signal indicates that the batteries 132 do not have sufficient charge to actuate the motor, main controller 380 inhibits all actuation of this pump. This prevents the pump from being set up for operation when it is not in a state in which it can fully discharge fluid.

Main controller 380 is also connected to the user interface 330 to actuate the LEDs integral with the interface.

A crystal 408 is also connected to main controller 380. Crystal 408 provides a constant frequency signal that is used as a clock pulse for purposes that will be described below.

Figure 30:
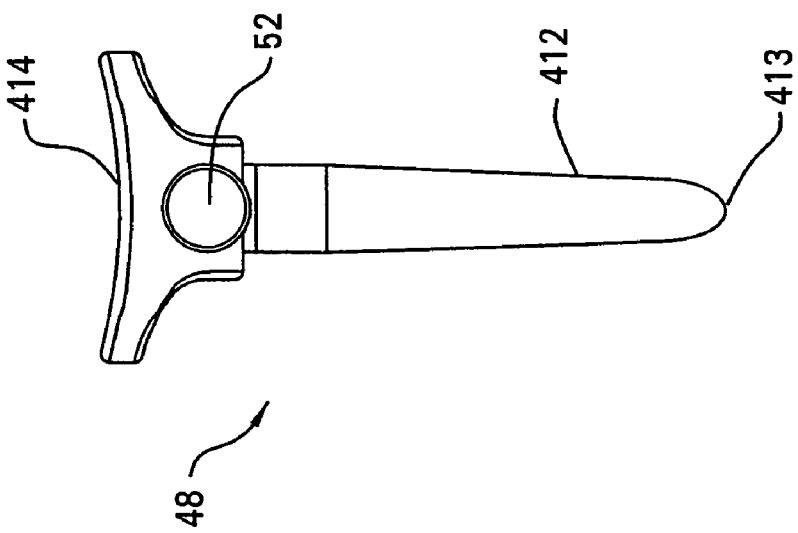
FIG. 30 is a rear view of the spike.
Figure 29:
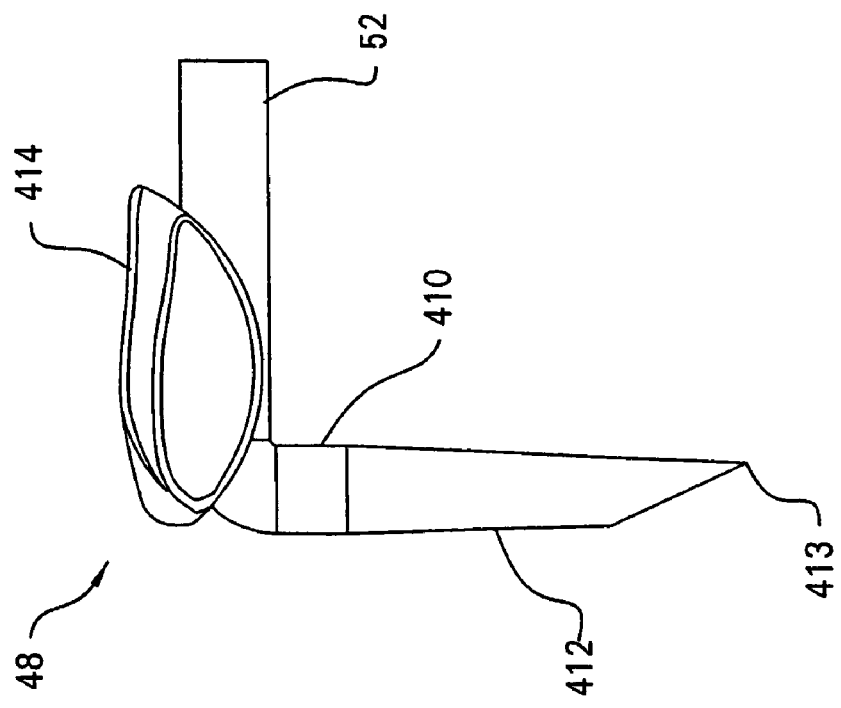
FIG. 29 is a side view of the tube set spike of this invention.

From FIGS. 29 and 30, it can be seen that spike 48 is formed to have an L-shaped tubular body 410. The vertical portion of the body 410 functions as the stem 412, the horizontally extending portion is the outlet spout 52. Spike body 410 is formed so that the tip of the stem 412 is beveled to a point 413. This shape facilitates the use of the body stem as a spike for inserting the spike 48 in a fluid bag 44. Spike body 410 is further formed so that the proximal end of the outflow tube 50 can be snugly fit over the spike spout 52.

Spike 48 is further formed to have thumb tab 414 that is integral with the body 410. Thumb tab 414 is positioned over the spike spout 52 immediately distal to the bend between the stem 412 and the spout 52. Thumb tab 414 serves as a member against which a person can push when inserting the spike stem 412 into a bag 44.

After a spike 48 is inserted in the bag 44 and the pump lid 42 is closed. The spike spout 52 and proximal end of the outflow tube 50 extend out between the pump spout 289 and the nose 258 of lid 42.

Occasionally, the cord 386 is plugged into a wall outlet in order to charge the batteries 132. While the batteries 132 are being charged, charger 388 actuates LED 358. When the batteries 132 are fully charged, battery charger 204 actuates LED 360. In some versions of the invention, as long as the cord 386 remains connected to the wall outlet, battery charger 388 provides a trickle charge to the batteries 132 so as to maintain the stored charge.

The operation of the pump 30 of this invention is now explained by reference to the flow charts of FIGS. 31A and 31B. Normally, when the pump is not being used, the pump is simply in the off state. When pump 30 is in this state, energization signals are not applied to the electrical components used to control the pump or the LEDs that provide information regarding the state of the pump. Pump 30 is normally in this state to minimize the drain on the batteries 132 when the pump is not used.

Figure 31A:
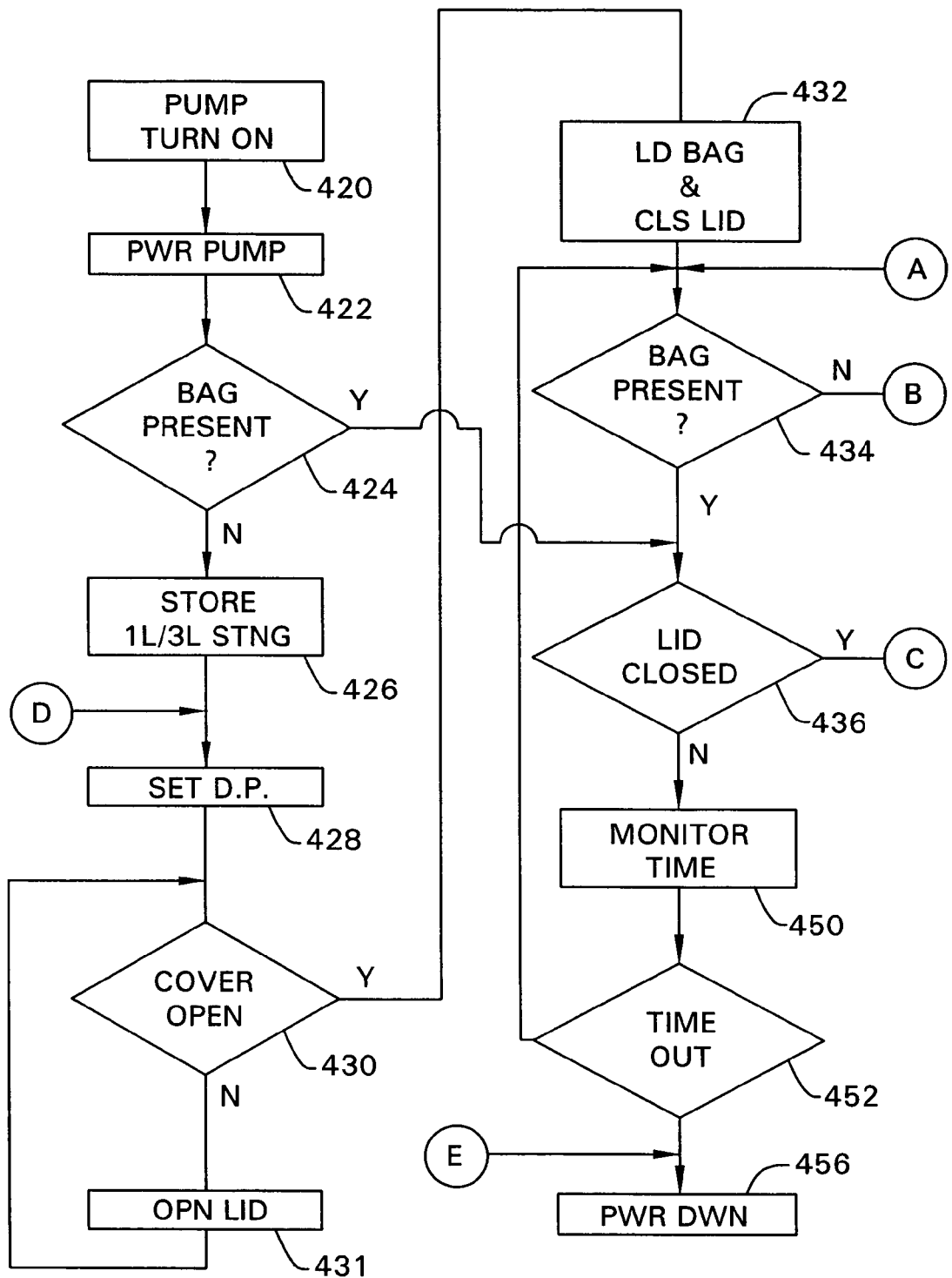
FIGS. 31A and 31B collectively form a flow chart of the major process steps executed during the operation of the pump.
Figure 31B:
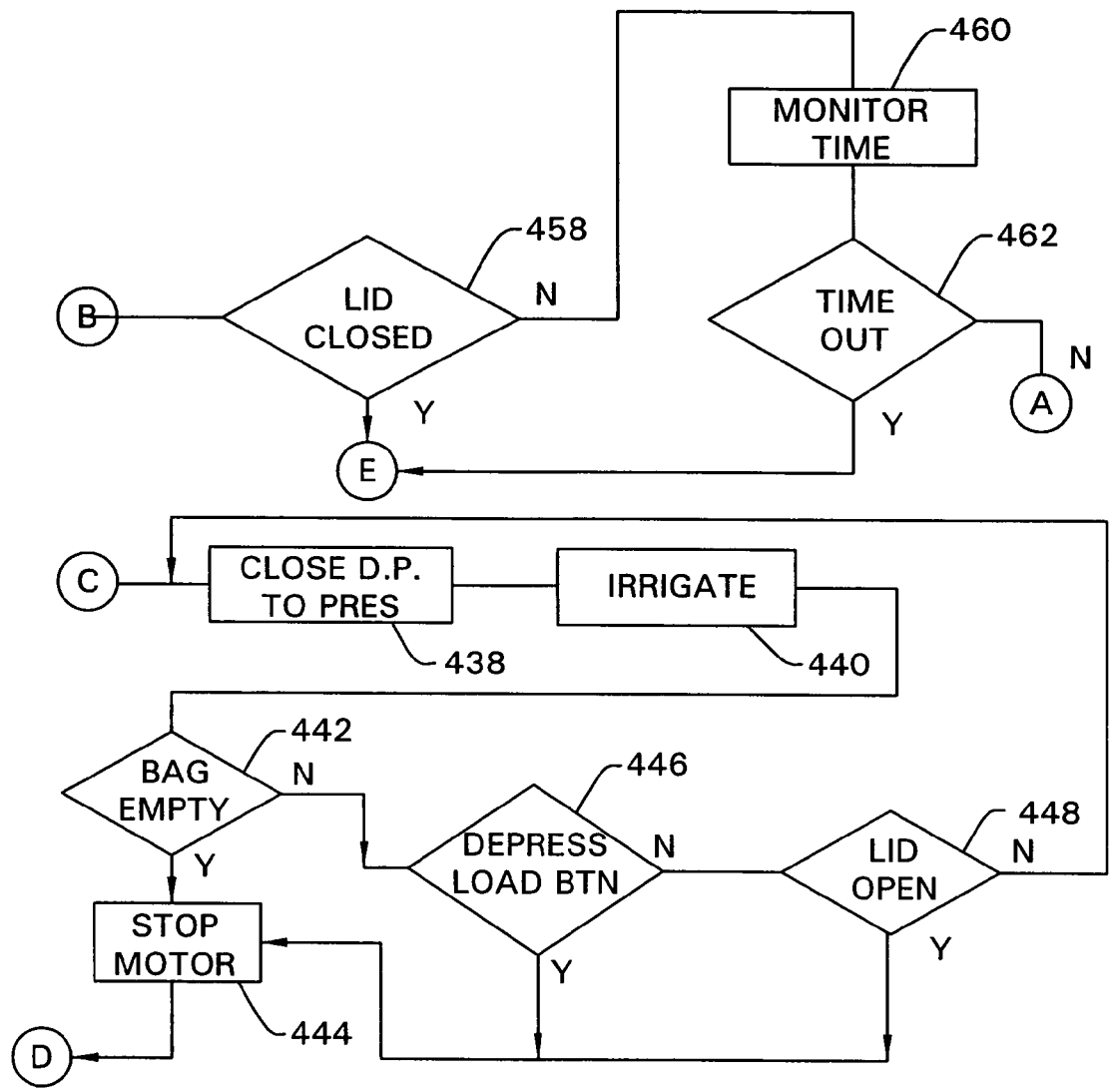

When the pump 30 is needed for use, medical personnel first perform a pump turn on step, step 420 in FIG. 31A. The pump turn on step 420 is performed by the medical personnel either closing the lid 42 or depressing the bag load switch 362. As described above, either action results in the assertion of the POWER_ON signal to the main controller 380. Main controller 380, upon receipt of the POWER_ON signal powers up the other components of the pump that are normally in the quiescent, non-power consuming state, step 422.

Once the pump components are fully powered, main controller 380 then reads the signal generated by the presence sensor 226 to determine whether or not a fluid bag 44 is disposed in the bag well 40, step 424. In most situations, the fluid bag from the last procedure in which pump 30 was employed will have been removed. Therefore, since there is no bag in the well 40, main controller 380 proceeds to execute a step 426, in which the main controller determines whether or not the 1 lt. or a 3 lt. bag 44 is to be fitted to the pump. This determination is made based on the data in the erasable memory internal to the controller based on the last depression of switch 340. Main controller 380 then actuates the motor 60, in a step 428, to ensure that the dynamic plate 38 is appropriately positioned so as to ensure that the space forming the bag well 40 is sized appropriately to receive the selected bag 44. The actual process steps performed by the main controller 380 to retract the dynamic plate are discussed below.

Once the dynamic plate 38 is appropriately positioned, main controller 380 reads the signal from switch 282, the LID_CLOSED signal, to determine whether or not the lid 42 is open or closed, step 430. If the lid 42 is closed, the main controller 380 opens the lid, step 431. The main controller 380 accomplishes this function by actuating solenoid 314 so as to cause the retraction of latch 298 away from hook 296. Once the latch 298 is so retracted, the torsion springs generate sufficient force to open lid 42.

Steps 430 and 431 are repeatedly executed until it is determined in step 430 that the lid is, in fact, open.

The pump 30 is now in a state in which medical personnel can place a fluid bag in well 40 and close the lid, represented by step 432 in FIG. 31A. Main controller 380 initially determines if these activities occurred by monitoring the output line from the bag presence sensor 226, step 434. If the BAG_YES signal from the bag presence sensor 226 indicates a bag has been placed in the well 40, main controller 380 then waits for a LID_CLOSED signal from switch 282 to determine whether or not the lid 42 is closed, step 436. Step 436 is also the step executed by the main controller 380 if, in step 424 it is determined upon power up of the pump that there was a bag in the well 40.

Once a fluid bag 44 is positioned in well 40 and lid 42 is closed, the pump 30 of this invention is ready for use. Main controller 380 actuates motor 60 so that the dynamic plate 38 is urged towards the static plate 36 until the BAG_PRESS signal from pressure sensor 228 indicates the bag is at a set pressure, step 438 in FIG. 31B. Fluid is then discharged from the pump by the medical personnel opening valve 54, represented in FIG. 18B as irrigation step 440. As fluid is discharged from the bag 44, bag pressure drops. Step 438 is continually executed by the main controller 380 to move the dynamic plate 38 towards the static plate 36. This movement maintains the bag pressure at the desired level. The maintenance of the bag pressure at the desired level ensures that, as long as the valve 54 is open and fluid is in the bag, the fluid will be discharged at the appropriate flow rate.

While the pump 30 is in operation, the dynamic plate 38 is displaced at an appropriate speed so as to maintain a select bag pressure. The selected bag pressure is a function of the user-selected flow rate. More particularly, the main controller 380 displaces the dynamic plate 38 to maintain a bag pressure that results in the desired flow rate out of the pump 30 when valve 54 is opened.

As the dynamic plate 38 moves toward the static plate 36, microswitches 216 send PLATE_POSITION signals to the main controller 380. Based on the received PLATE_POSITION signals, the main controller selectively actuates one of the LEDs 364a, b, c, d, e or f to provide an indication of the volume of fluid left in the bag 44.

Eventually, the movement of the dynamic plate 38 towards the static plate 36 results in the emptying of bag 44. Main controller 380 senses the complete emptying of the bag by the receipt of a PLATE_POSITION signal from one of the microswitches 216 indicating that the dynamic plate 38 has closed against the static plate 36. This is represented by the bag empty determination step 442. When this event occurs, main controller 380 stops the actuation of the motor 60 to prevent further movement of the dynamic plate 38, step 444. Once the bag 44 is so emptied, main controller 380 re-executes step 428, and the subsequent steps, so the empty bag can be removed and a full bag loaded.

Sometimes, all the fluid in the bag 44 is not used during the surgical procedure. In this instance, the surgical personnel depress the bag load switch 362. The detection of the depression of this switch, and the resultant application of the BAG_LOAD signal to the main controller 380 is depicted in FIG. 31B by main controller 380 executing step 446. This step is executed if, in step 442, it is determined that the bag is not empty. If, in step 446, it is determined that the bag load switch 362 is depressed, steps 444, 428 and the subsequent steps thereafter are re-executed.

While fluid is being discharged from the pump 30, main controller 380 also monitors switch 282 to determine whether or not the lid 42 is inadvertently opened. This is represented in FIG. 31B by the execution of step 448 after the execution of step 446. If this condition is detected, steps 444, 428 and the subsequent steps, are re-executed.

If, however, during the extension of the dynamic plate 38, it is determined the bag 44 has not been emptied, the bag load switch 328 has not been depressed, and the lid 42 has not been opened, the main controller continues to actuate motor 60, execute step 438, to maintain the appropriate pressure on the fluid bag 44.

After a fluid bag 44 is placed in well 40, main controller 380 monitors the amount of time that elapses before the lid is closed. This monitoring, step 450 in FIG. 31A, is performed after step 436.

In step 452, the main controller 380 determines whether or not the lid has been allowed sit open for a fixed time period. This time period is typically less than 10 minutes. As long as the time period is within this time period, main controller 380 continually re-executes steps 434 and 436 to continually verify that there is a fluid bag 44 in well 40 and the lid 42 is closed.

However, in step 452, it may be determined that the pump 30 has not been actuated for the set period of time. If this event occurs, main controller 380 proceeds to a power down step 456. In the power down step 456, the main controller 380 denergizes the power consuming components of the pump to reduce the drain on batteries 132. As part of the power down step 456, main controller 380 powers down the main controller 380.

Pump 30 is reactivated by the user again pressing the bag load switch 362 so as to cause the re-execution of step 420.

In step 436, there is a possibility the user may simply close the lid 42 without placing a bag in well 40. The placement of pump 30 in this state is detected by the sequential execution of steps 438 and 458. If the user places the pump 30 in this state, it is assumed that use of the pump is no longer required. Main controller 380 then executes the power down step 456.

After the lid 42 is opened in step 431, there is a possibility the user will neither place a fluid bag in the well 40 nor close the lid. In other words, the user does not perform process step 266. Main controller 380 determines whether or not the pump 30 is in this state by the execution of steps 434 and 458. If the pump is in this state, the main controller 380, in steps 460 and 462, monitors how long the pump 30 is in this state. If the pump 30 remains in this state for a set period, typically 10 minutes or less, the main controller 380, executes the power down step 456.

Figure 32:
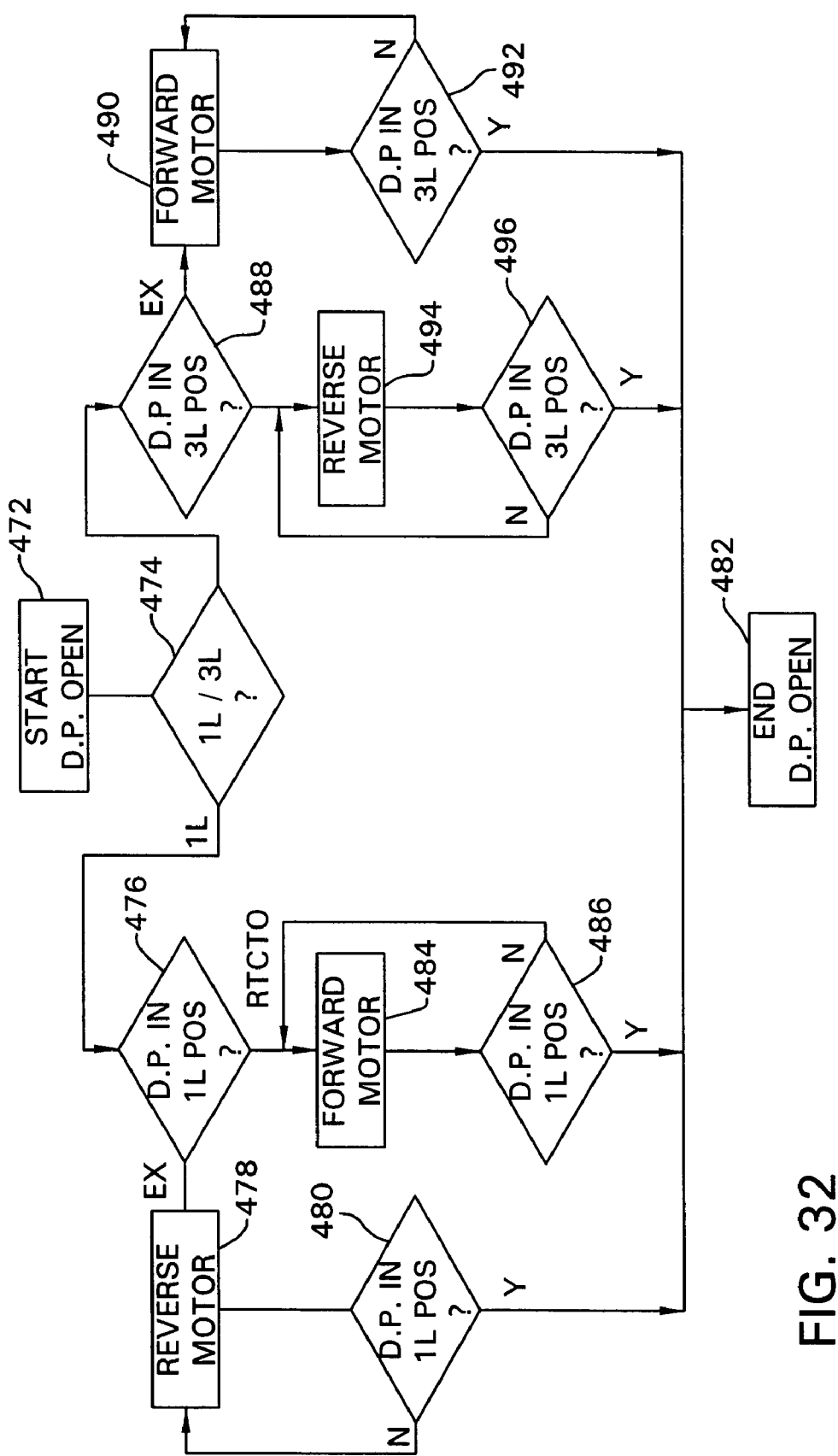
FIG. 32 is a flow chart of the process steps that are executed in order to position the dynamic plate so that the pump is configured to receive a fluid bag.

FIG. 32 illustrates the process by which the dynamic plate 38 is retracted, step 428 in FIG. 31A. The start of the process for opening the dynamic plate is represented by step 472. After this step, the state of the switch 226 that indicates whether or not a 1 lt. or 3 lt. fluid bag 44 is to be fitted to the pump is read, step 474. Step 474, it should be understood, is performed by reading the data stored in the memory internal to the main controller 380.

If the stored data indicate a 1 lt. fluid bag is to be fitted to the pump, the main controller, in step 476, determines from the PLATE_POSITION signals if the dynamic plate is retracted away from or extended beyond the position for receiving the 1 lt. bag. If the dynamic plate 38 is extended beyond the position for receiving the 1 lt. bag, the main controller 380, in step 478, reverses motor 60 to retract the dynamic plate 38 away from the static plate 36. While the dynamic plate 38 is being retracted, main controller 380 continues to monitor the PLATE POSITION signals, step 480. As soon as the PLATE POSITION signals indicate that dynamic plate 38 is positioned so the bag well 40 can receive a 1 lt. bag, the main controller 380 stops the actuation of the motor 60. In FIG. 32, this is represented by the end dynamic plate open step 482.

Alternatively, in step 476, it may be determined that the dynamic plate is retracted beyond the position in which the pump is configured to receive the 1 lt. bag 44. Then, main controller 380, in step 484, causes motor 60 to operate in the forward direction so as to extend the dynamic plate 38. While the dynamic plate 38 is being so displaced, the main controller 380 continues to monitor the PLATE POSITION signals until they indicate the dynamic plate 38 is appropriately positioned, step 486. Once this event occurs, the motor 60 is deactivated, step 482 is executed.

The user may indicate that a 3 lt. bag is to be inserted in the pump 30. If this determination is made in step 474, main controller 380, in step 488 determines from the PLATE_POSITION signals if the dynamic plate 38 is positioned so that well 40 can receive a 3 lt. bag. If, in step 488 it is determined that the dynamic plate 38 is retracted beyond the position for receiving the 3 lt. bag, the main controller in step 490 causes the motor 60 to run in the forward direction. The motor 60 is so actuated until, in a step 492, it is determined from the PLATE POSITION signals that dynamic plate 38 is appropriately positioned so the pump can receive a 3 lt. bag. Once this event occurs, step 482 is executed so as to deactivate the motor.

Alternatively, it may be determined in step 388 that the dynamic plate 38 is extended beyond the position in which the pump can accept a 3 lt. bag. If the dynamic plate 38 is so positioned, main controller 380, in step 494, causes motor 60 to reverse so as to retract the dynamic plate 38. The dynamic plate 38 is retracted until, in a step 324, the PLATE_POSITION signals indicate that the dynamic plate 38 is appropriately positioned so the bag well 40 can receive a 3 lt. bag, step 496. Once the dynamic plate 38 is so retracted, step 482 is executed so as to deactuate the motor and stop the movement of the dynamic plate.

Irrigation pump 30 is able to provide irrigating fluid at relatively high flow rates, between 2 and 4 lt./min. The power to actuate the pump comes from rechargeable batteries 132. Thus, in order to use the pump 30 during a surgical procedure, it does not need to be connected to a source of power such as a compressed air source or a wall outlet. This means that when the pump 30 is employed in a surgical procedure, one does not need to provide an electrical cord or an air line to connect the pump to the external power source.

The hardware and software integral with the pump 30 automatically set the position of the dynamic plate 38 and lid 42, so that the pump is ready to receive a fluid bag 44. Once the fluid bag 44 is placed in the bag well 40 all the user has to do is close the lid 42. Again, the components internal to the pump automatically configure themselves to quickly make the pump ready for use. More specifically, once a user presses the bag load switch 224, the pump can be configured for operation in 10 seconds or less. Thus, the pump 30 of this invention is further designed to minimize the amount of time and attention the user is required to spend making the pump ready for operation.

Pump 30 is further designed to inhibit operation if there is human error in the setting up of the pump. Specifically, when the pump is configured to operate with a 1 lt. bag, the position of the dynamic plate 38 is such that a person cannot inadvertently place a 3 lt. bag in the bag well 40. If, when the pump is configured to receive a 3 lt. bag, a 1 lt. bag is placed in the well, the top of the bag will be below the bag presence sensor 226. Thus, if the pump is so misconfigured for operation, the bag presence sensor will not generate the requisite BAG_YES signal required to actuate the pump 30. This would prompt the medical personnel to investigate when the cause of the malfunction and correct the situation.

It should similarly be understood that said pump is further configured so that main controller 380 will not actuate motor 60 unless the LID_CLOSED signal from microswitch 282 indicates the lid 42 is closed. This feature of the pump 30 of this invention substantially eliminates the possibility that a person's limb or article of clothing will be caught in the bag well 40 when the pump is actuated and the dynamic plate 38 closes towards the static plate 36. For the same reason, the main controller 380 is configured to only assert the SLND signal to cause the unlocking of the lid 42, when the motor 60 is not being actuated.

When pump 30 is in use, LEDs 364 provide easy to see indications of the extent to which the dynamic plate 38 is extended towards the static plate 36. Thus, during the performance of a surgical procedure, medical personnel can quickly ascertain whether or not there is sufficient fluid in bag 44 to accomplish the desired surgical task.

It should be recognized that the above description is directed to one particular version of the pump 30 of this invention. Other versions of the pump 30 may have alternate features.

For example, alternative linkages other than the described gear and shaft assembly may be used to extend/retract the dynamic plate 38. For example, in some versions of the invention, the output shaft of the motor may be directly connected to a gear or other member that actually displaces the dynamic plate 38. There is no requirement that, in all versions of the invention, motor 60 stay with the static plate. In some versions of the invention, motor 60 and the associated transmission system may be dynamic mounted components. Also, there is no requirement that, in all versions of the invention, the transmission system be a gear system. In some versions of the invention, pump 30 may contain a small hydraulic drive system. In these versions of the invention, motor 60 would drive a small hydraulic pump. This hydraulic pump supplies pressurized fluid to a piston or pistons that selectively displace the dynamic plate.

Similarly, it should be recognized that, the relative arrangement of the static and dynamic plates is illustrative, not limiting. In some versions of the invention, the static plate may be the plate that is closest to the bracket or other fixed skeletal member of the pump. In these versions of the invention, the pump 30 is configured so that, in order to force fluid from the attached bag, the dynamic plate retracts towards the static plate. Once the fluid bag is empty, the hardware and software of the pump are set to extend the dynamic plate away from the static plate.

Also, there is no requirement that, in all versions of the invention, the dynamic plate be pivotally connected to the static components of the pump. In some versions of the invention, it may be desirable to construct the pump so that the dynamic plate is parallel aligned with the static plate. In these versions of the invention, an appropriate linkage mechanism displaces the dynamic plate so that it moves in a linear path of travel towards and away from the static plate.

It should be understood that, in some versions of the invention, both of the plates between which the fluid bag is placed will move relative to static components of the pump. In these versions of the invention, some type of scissors linkage may move the plates together simultaneously whenever fluid is to be discharged from the pump. Alternatively, in these versions of the invention, it may be desirable to provide the pump with two independently operated drive assemblies each of which independently actuates one of the plates. In these versions of the invention, whenever fluid is to be discharged at a relatively slow rate from the pump, only a single one of the drive mechanisms is actuated to displace a single one of the plates toward the second plate. In situations wherein fluid is to be discharged from the pump at relatively high rates, the drive mechanisms are actuated simultaneously. The plates are thus simultaneously moved toward each other to force the rapid discharge of fluid.

Furthermore, the electrical components integral with this pump may be different from what has been described. For example, means other than the described switches 216 may be provided to generate signals representative of the relative positions of the plates 36 and 38 to each other. For instance, in some versions of the invention a potentiometer may perform this function. In these versions of the invention, the wiper of the potentiometer is geared to one of the drive shafts that displace the dynamic plate 38. The resistance of the potentiometer thus provides an indication of the position of the dynamic plate. An advantage of this version of the invention is that the output signal from the potentiometer provides a continuous indication of the present position of the dynamic plate. It may also be possible to provide the dynamic plate 38 with some member that can be readily viewed through a window in the cabinet. By viewing this member the surgical personnel can determine the extent to which the plate is extended/retracted.

In still other versions of the invention, a Hall sensor and a complementary magnet may be used to collectively provide a signal representative of the instantaneous position of the dynamic plate 38. In these versions of the invention, one of the Hall sensor or the magnet is mounted to a static component of the pump. The remaining one of these components is mounted to the dynamic plate. In these versions of the invention, the output signal of the Hall sensor varies with the proximity of the magnet to the sensor.

In the above versions of the invention, it may still be desirable to provide one or more limit switches. These switches provide signals indicating when the dynamic plate is in its fully extended and/or fully retracted position. Thus the output signals from the switches are employed as a failsafe to prevent the actuation of the motor 60 when the plate cannot be displaced.

Alternative sensors may be incorporated into other versions of this invention. For example, the bag presence sensor may not include a mechanical member that is physically deflected. In some versions of the invention, the bag presence sensor may include some type of photosensitive assembly with complementary light source. The light source emits a wavelength of light that is absorbed by the bag or its contents. The output signal from the detector that monitors the presence/absence of the light generates the BAG_YES signal. Alternatively, some type of pressure sensitive transducer may be employed as the bag presence sensor. In some versions of the invention a single sensor may provide an output signal that functions as both the signal indicating the presence/absence of the fluid bag and the bag pressure.

Similarly, in some versions of the invention, a single solenoid and complementary linkage may both hold the lid 42 in the closed state and, upon actuation of the solenoid, open the lid.

The disclosed process steps executed in order to operate the pump are also understood to be exemplary, not limiting. For example, some versions of the invention may be configured so that after the bag 44 is placed in the well 40 and the lid 42 is closed, the user is required to depress an "operate" switch. Only after this switch is depressed does the pump set the dynamic plate to the appropriate position. This version of the invention thus requires the user to provide in one more acknowledgments before the pump is ready for use.

Likewise, it should be recognized that the system may be provided with some sort of tone or programmed speech generator. This generator would provide audible tones or messages that the pump is in a certain condition such as fully charged, bag in place and ready for use, bag partially empty, bag empty or battery low.

It should further be recognized that the above-described pump is intended to be used with either 1 lt. or 3 lt. fluid bag is merely descriptive, not limiting. Some versions of the pump of this invention may be designed for use with a single sized fluid bag. Still it may be desirable to provide other versions of this invention that are configured for use with three or more different sized fluid bags.

In some versions of this invention, the pump may have a head capable of reading an RFID chip. Such a chip is attached to the bag. The data in this chip identifies the volume of the bag and the maximum and minimum flow rates at which fluid can be discharged from the bag. Then, upon the bag being placed in the bag well, the data in the RFID chip are read from the chip. The pump main controller then configures the pump so that fluid is discharged in accordance with the bag-specific data.

Therefore, it should be recognized that it is an object of the appended claims cover all such variations and modifications of the invention as come within the true sprit and scope of the invention.

What is claimed is:

1. A surgical irrigation pump arrangement comprising:
   a cabinet, said cabinet having an opening;
   first and second plates disposed in said cabinet, said first plate being movable towards and away from said second plate so as to define a varying volume bag well between said first and second plates, said varying volume bag well being accessible through said opening in said cabinet;
   a drive assembly disposed in said cabinet and attached to said first plate for moving said first plate;
   a user interface including a bag-size control configured for actuation by a user to allow selection of a first fluid bag size or a second fluid bag size of a different volume than a volume of the first fluid bag size;
   a control unit in communication with said bag-size control and connected to said drive assembly, said control unit actuating said drive assembly to move said first plate to a first position wherein said first plate is spaced from said second plate a first distance sufficient to accommodate the first fluid bag size in said varying volume bag well when said bag-size control indicates a user selection of the first fluid bag size, said control unit actuating said drive assembly to move said first plate to a second position wherein said first plate is spaced from said second plate a second distance different from the first distance and sufficient to accommodate the second fluid bag size in said varying volume bag well when said bag-size control indicates a user selection of the second fluid bag size, said control unit actuating said drive assembly to move said first plate towards said second plate to compress a fluid bag disposed in said varying volume bag well, said control unit preventing operation of said drive assembly when the first fluid bag size is selected and said first plate is in said first position and a user attempts to place a fluid bag corresponding to the second fluid bag size in said varying volume bag well, and said control unit preventing operation of said drive assembly when the second fluid bag size is selected and said first plate is in said second position and a fluid bag corresponding to the first fluid bag size is located in said varying volume bag well.

2. The pump arrangement of claim 1, wherein both said first plate and said second plate are attached to said drive assembly and configured to move towards and away from one another so as to define said varying volume bag well between said first and second plates.

3. The pump arrangement of claim 1, further comprising:
   a lid moveably attached to said cabinet and selectively positionable in a closed position wherein said lid closes said opening in said cabinet and an open position wherein said lid is spaced from said opening; and
   a lid state sensor attached to said cabinet for monitoring an open/closed state of said lid;
   wherein said control unit is in communication with said lid state sensor, said control unit being configured to allow actuation of said drive assembly only when said lid state sensor indicates that said lid is in the closed position.

4. The pump arrangement of claim 3, wherein:
   said cabinet defines a recessed surface forming part of said opening and dimensioned to accommodate an outflow tube extending through said opening; and
   said lid is formed with a nose that, when said lid is in the closed position, extends over but is spaced from said recessed surface.

5. The pump arrangement of claim 3, further comprising:
   a latch moveably mounted to said cabinet for holding said lid in the closed position; and
   a latch actuator disposed in said cabinet and connected to said latch for selectively moving said latch away from said lid to allow said lid to move into the open position;
   wherein said control unit is connected to said latch actuator for causing said latch actuator to move said latch away from said lid, and said control unit is further configured to only actuate said latch actuator to move said latch away from said lid when said drive assembly is not being actuated.

6. The pump arrangement of claim 3, further comprising:
   a biasing member extending between said cabinet and said lid for normally urging said lid into the open position away from said opening in said cabinet;
   a latch moveably mounted to said cabinet for holding said lid in the closed position; and
   a latch actuator disposed in said cabinet and connected to said latch for selectively moving said latch away from said lid;
   wherein said control unit is connected to said latch actuator for causing said latch actuator to move said latch away from said lid, and said control unit is further configured to only actuate said latch actuator when said drive assembly is not being actuated.

7. The pump arrangement of claim 1, wherein said second plate is statically connected to said cabinet.

8. The pump arrangement of claim 1, wherein an end of said first plate is pivotally connected to said second plate.

9. The pump arrangement of claim 1, wherein:
   said drive assembly includes a motor and a gear assembly connected to said motor; and
   said motor and said gear assembly are attached to said first plate so as to move with said first plate.

10. The pump arrangement of claim 1, wherein:
    a pressure sensor is mounted to one of said first plate or said second plate and is positioned to extend into said varying volume bag well to monitor the pressure of a fluid bag in said varying volume bag well and generate a variable signal as a function of a sensed pressure in the fluid bag;
    said drive assembly is configured to move said first plate toward said second plate at a variable speed;
    said control unit receives from said pressure sensor the signal and is further configured to, in response to the signal, regulate a speed at which said drive assembly causes said first plate to move towards said second plate.

11. The pump arrangement of claim 1, wherein:
    said drive assembly includes an electrically actuated motor;
    a rechargeable battery pack is located in said cabinet for providing power to said electrically actuated motor; and a battery charger is disposed in said cabinet for receiving a line current and charging said rechargeable battery pack with a charging current.

12. The pump arrangement of claim 1, wherein said first plate in said second position is spaced from said second plate a distance greater than a distance said first plate is spaced from said second plate in said first position and the second fluid bag size is greater than the first fluid bag size, said pump arrangement comprising a bag presence sensor disposed in said cabinet adjacent said varying volume bag well for detecting the presence of a fluid bag in said varying volume bag well, said bag presence sensor generating a signal upon detecting a fluid bag in said varying volume bag well, said bag presence sensor being positioned in said cabinet so that, when said first plate is in said second position and a fluid bag corresponding to the first fluid bag size is located in said varying volume bag well, said bag presence sensor does not detect the presence of the fluid bag and said control unit prevents operation of said drive assembly.

13. The pump arrangement of claim 12, wherein said control unit is connected to said bag presence sensor for receiving the signal and is further configured to regulate said drive assembly based on whether the signal indicates a fluid bag is in said varying volume bag well.

14. The pump arrangement of claim 1, further comprising a lid moveably attached to said cabinet and positionable in an open position wherein said lid is spaced from said opening and a closed position wherein said lid closes said opening, said lid in the closed position being oriented transversely to both of said first plate and said second plate.

15. A surgical pump, said pump including:
a cabinet, said cabinet having an opening;
a first plate and a second plate disposed in said cabinet, said first plate and said second plate being positioned so as to define a bag well in said cabinet between said first plate and said second plate, said bag well being accessible through said opening, said first plate being displaceable towards and away from said second plate into:
  a first open position wherein said first plate and said second plate are spaced from one another a distance sufficient to accommodate a first fluid bag containing a first volume of fluid in said bag well; and
  a second open position wherein said first plate and said second plate are spaced from one another a distance sufficient to accommodate a second fluid bag containing a second volume of fluid larger than the first volume of fluid in said bag well;
a bag presence sensor disposed in said cabinet for monitoring the presence/absence of a fluid bag in said bag well and that generates a signal representative of the presence/absence of a fluid bag in said bag well, said bag presence sensor being positioned so that when said first plate is in the second open position and a first fluid bag is in said bag well, said bag presence sensor is unable to detect the presence of the first fluid bag;
a drive assembly disposed in said cabinet and attached to said first plate for displacing said first plate towards and retracting said first plate away from said second plate; and
a control unit connected to said bag presence sensor for receiving the signal, and connected to said drive assembly for controlling actuation of said drive assembly, said control unit regulating actuation of said drive assembly based on whether the signal from said bag presence sensor indicates the presence of a fluid bag in said bag well, said control unit preventing actuation of said drive assembly and operation of said pump when the signal from said bag presence sensor indicates that no fluid bag is present in said bag well.

16. The surgical pump of claim 15, wherein said drive assembly includes a motor disposed in said cabinet.

17. The surgical pump of claim 15 wherein said drive assembly includes:
a motor having a drive shaft, said motor being attached to said first plate to move with said first plate;
a gear assembly attached to said first plate to move with said first plate, said gear assembly including at least one pinion gear and configured to receive rotational power from said drive shaft so that the power from said drive shaft rotates said at least one pinion gear; and
a rack statically mounted on said second plate in said cabinet, wherein said rack is positioned so that said at least one pinion gear engages said rack so that rotation of said at least one pinion gear causes movement of said first plate toward said second plate.

18. The surgical pump of claim 15, wherein:
a pressure sensor is mounted to one of said first plate or said second plate and is positioned to extend into said bag well to monitor the pressure of a fluid bag in said bag well and generate a variable signal as a function of a sensed bag pressure in the fluid bag;
said drive assembly is configured to move said first plate toward said second plate at a variable speed, said control unit receiving from said pressure sensor the signal, and in response to the signal, regulating the speed at which said drive assembly causes said first plate to move towards said second plate.

19. The surgical pump of claim 15, wherein said first plate and said second plate are pivotally connected together.

20. The surgical pump of claim 15, wherein said second plate is statically mounted to said cabinet.

21. The surgical pump of claim 15, wherein said bag presence sensor is mounted to one of said first plate or said second plate.

22. The surgical pump of claim 21, wherein said drive assembly includes a motor mounted to said first plate that is displaceable so as to move with said first plate.

23. The surgical pump of claim 15, wherein said bag presence sensor is disposed in said cabinet to contact the second fluid bag when the second fluid bag containing the second volume of fluid is placed in said bag well and said first plate is in said second open position, and said bag presence sensor is disposed in said cabinet so as to not contact the first fluid bag when the first fluid bag containing the first volume of fluid is placed in said bag well and said first plate is in said second open position, and said bag presence sensor is disposed in said cabinet so as to contact the first fluid bag when the first fluid bag containing the first volume of fluid is placed in said bag well and said first plate is in said first open position.

24. The surgical pump of claim 23, wherein said bag presence sensor is disposed on said first plate in said bag well.

25. A surgical pump comprising:
a cabinet;
a first plate and a second plate disposed in said cabinet, said first plate and said second plate defining a bag well therebetween;
a drive assembly connected to said first plate for effecting relative movement between said first plate and said second plate to increase or reduce a volume of said bag well;
a control unit connected to said drive assembly and including a control circuit configured to actuate said drive assembly to position said first plate relative to said second plate in:

a first position defining a first volume of said bag well wherein a first fluid bag containing a first volume of fluid can be fully received in said bag well; and a second position defining a second volume of said bag well wherein said first fluid bag or a second fluid bag containing a second volume of fluid greater than the first volume of fluid and exceeding said first volume of said bag well can be fully received in said bag well; and a bag presence sensor in communication with said control unit and located in a position in said bag well for detecting the presence of a fluid bag in said bag well and sending a bag presence signal to said control unit, said bag presence sensor being located in a position in said bag well so as to be incapable of detecting the first fluid bag in said bag well when said first plate is in the second position such that said bag presence sensor does not send a bag presence signal to said control unit and said control unit prevents operation of said pump.

26. The pump of claim 25, wherein said control circuit of said control unit is configured to actuate said drive assembly only upon receiving a bag presence signal from said bag presence sensor.

27. The pump of claim 25, wherein said bag presence sensor is located in said bag well in a position which allows said bag presence sensor to detect the presence of the first fluid bag in said bag well when said first plate is in the first position.

28. The pump of claim 25, wherein said cabinet comprises:

an opening and a lid connected to said cabinet for movement between an open position wherein said lid is spaced from said opening and a closed position wherein said lid covers said opening;

a latch engageable with said lid to secure said lid in the closed position; and a latch actuator connected to said latch and controlled by said control unit, wherein said control unit locks said latch actuator to maintain said lid in the closed position when said drive assembly is effecting a reduction in the volume of said bag well.

29. The pump of claim 28, wherein said control unit unlocks said latch actuator to disengage said latch from said lid and allow said lid to move into the open position and allow said drive assembly to effect an increase in the volume of said bag well.

* * * * *